United States Patent [19]

Melloni et al.

[11] Patent Number: 5,721,227
[45] Date of Patent: *Feb. 24, 1998

[54] 17-ARYL AND 17-HETEROCYCLYL-14β-5α-ANDROSTANE, ANDROSTENE AND ANDROSTADIENE DERIVATIVES ACTIVE ON THE CARDIOVASCULAR SYSTEM, PROCESSES FOR THEIR PREPARATION AND PHARMACEUTICAL COMPOSITIONS CONTAINING SAME

[75] Inventors: Piero Melloni, Bresso; Luigi Bernardi, Milan; Mara Ferrandi, Milan; Marco Frigerio, Milan; Marina Mauro, Milan; Luisa Quadri, Cernusco, all of Italy

[73] Assignee: Sigma-Tau Industrie Farmaceutiche Riunite S.p.A., Rome, Italy

[*] Notice: The term of this patent shall not extend beyond the expiration date of Pat. No. 5,569,694.

[21] Appl. No.: 552,796

[22] Filed: Nov. 3, 1995

Related U.S. Application Data

[62] Division of Ser. No. 128,116, Sep. 29, 1993, Pat. No. 5,556,846.

[30] Foreign Application Priority Data

Sep. 29, 1992 [DE] Germany ............... 42 32 681.8

[51] Int. Cl.$^6$ .................... A61K 31/58; C07J 43/00; C07J 17/00
[52] U.S. Cl. .................... 514/172; 514/176; 540/94; 540/95; 540/101
[58] Field of Search ............... 540/94, 95, 101; 514/172, 176, 177, 182; 552/612, 623

[56] References Cited

U.S. PATENT DOCUMENTS 5,567,694  10/1996  Almirante et al. .............. 514/169

*Primary Examiner*—Mukund J. Shah
*Assistant Examiner*—Bruck Kifle
*Attorney, Agent, or Firm*—Oblon, Spivak, McClelland, Maier & Neustadt, P.C.

[57] ABSTRACT

17-Aryl -5α,14β-androstane, androstene and androstadiene derivatives of formula (I):

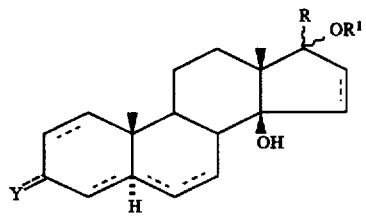

wherein the symbol --- represents a single or a double bond; when the double bond is not present in the 4 or 5 position, the hydrogen in position 5 has the α configuration;

Y is oxygen or guanidinoimino, when --- in position 3 is a double bond;

Y is hydroxy, $OR^2$ or $SR^2$, when in position 3 is a single bond and has an α or β configuration;

R is a substituted or unsubstituted aryl ring; and $R^1$ is hydrogen, methyl, ethyl or n-propyl substituted by OH or $NR^4R^5$.

4 Claims, No Drawings

17-ARYL AND 17-HETEROCYCLYL-14β-5α-ANDROSTANE, ANDROSTENE AND ANDROSTADIENE DERIVATIVES ACTIVE ON THE CARDIOVASCULAR SYSTEM, PROCESSES FOR THEIR PREPARATION AND PHARMACEUTICAL COMPOSITIONS CONTAINING SAME

This is a division of application Ser. No. 08/128,116 filed on Sep. 29, 1993, now U.S. Pat. No. 5,556,846.

The present invention relates to 17-aryl and 17-heterocyclyl-5α,14β-androstane, androstene and androstadiene derivatives, active on the cardiovascular system, to a process for their preparation and to pharmaceutical compositions containing same for the treatment of cardiovascular disorders such as heart failure and hypertension.

The invention relates to compounds of formula (I):

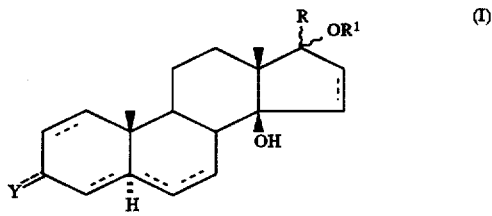

wherein:

the symbol ⤳ means that the substituents in position 17 can have an α or β configuration;

the symbol --- represents a single or a double bond; when the double bond is not present in the 4 or 5 position, the hydrogen in position 5 has the α configuration;

Y is oxygen or guanidinoimino, when --- in position 3 is a double bond;

Y is hydroxy, $OR^2$ or $SR^2$, when --- in position 3 is a single bond and can have an a or D configuration;

R is an aryl ring or a saturated or unsaturated mono- or bi-heterocyclic ring, containing one or more heteroatoms chosen from the group of oxygen, sulfur and nitrogen, unsubstituted or substituted by one or more halogen, hydroxy, hydroxymethyl, alkoxy, oxo, amino, alkylamino, dialkylamino, cyano, nitro, sulfonamido, C1–C6 lower alkyl group or $COR^3$;

$R^1$ is hydrogen; methyl; ethyl or n-propyl substituted by OH or $NR^4R^5$;

$R^2$ is hydrogen; methyl: C2–C6 alkyl or C3–C6 alkenyl or C2–C6 acyl, unsubstituted or substituted by a quaternary ammonium group or one or more $OR^6$, $NR^7R^8$, CHO, C(NH)NH$_2$, guanidinoimino or by $NR^7R^8$ and hydroxy;

$R^3$ is hydrogen, hydroxy, C1–C4 alkoxy or C1–C4 alkyl;

$R^4$, $R^5$ are independently hydrogen; methyl; C2–C6 alkyl unsubstituted or substituted by $NR^9R^{10}$, or $R^4$ and $R^5$ taken together with-the nitrogen atom form an unsubstituted or substituted saturated or unsaturated five- or six- membered heterocyclic ring, optionally containing another heteroatom chosen from oxygen or sulfur or nitrogen;

$R^6$ is hydrogen; methyl; C2–C4 alkyt unsubstituted or substituted by one or more $NR^9R^{10}$ or by $NR^9R^{10}$ and hydroxy;

$R^7$, $R^8$ are independently hydrogen; methyl; C2–C6 alkyl or C3–C6 alkenyl unsubstituted or substituted by one or more $NR^9R^{10}$, or $NR^9R^{10}$ and hydroxy, or $R^7$ and $R^8$ taken together with the nitrogen atom form an unsubstituted or substituted saturated or unsaturated five- or six- membered heterocyclic ring, optionally containing another heteroatom chosen from oxygen or sulfur or nitrogen, or $R^7$ is hydrogen and $R^8$ is C(NH)NH$_2$;

$R^9$, $R^{10}$ are independently hydrogen, C1–C6 alkyl, or $R^9$ and $R^{10}$, taken together with the nitrogen atom they are linked to form a saturated or unsaturated five- or six-membered heterocyclic ring.

The invention includes within its scope all the possible stereoisomers, in particular Z and E isomers, optical isomers and their mixtures and the metabolites and the metabolic precursors of the compounds of formula (I).

Also included in this invention are pharmaceutically acceptable salts of (I), which retain the biological activity of the base and are derived from known pharmacologically acceptable acids such as hydrochloric, sulfuric, phosphoric, malic, tartaric, maleic, citric, methanesulfonic or benzoic acid.

When R is an aryl ring it is preferably phenyl or naphtyl unsubstituted or substituted preferably by methyl, ethyl, isopropyl, methoxy, halide, cyano, nitro, sulfonamido, arnino, dimethylamino, carboxy, dicarboxy, di(methoxycarbonyl), di(hydroxymethyl).

When R is a saturated or unsaturated heterocyclic ring it is preferably 1,3-dithian-2-yl, furyl, tetrahydrofuryl, thienyl, pyrrolyl, pyridyl, pyridyl-N-oxide, pyrimidinyl, pyridazinyl, piperidyl, pyrazolyl, imidazolyl, methylimidazolyl, imidazolinyl, thiazolyl, oxazolyl, oxazolinyl, isoxazolyl, triazolyl, 2-oxo-(1H)-pyridyl, 2-oxo-(2H)-5-pyranyl, 2-oxo-(5H)-4-pyrrolyl.

The alkyl and alkenyl groups may be branched or straight chain groups.

The C1–C6 alkyl group is preferably a C1–C4 alkyl group, e.g. methyl, ethyl, n-propyl./so-propyl, n-butyl, sec-butyl.

The C2–C6 alkyl group is preferably a C2–C4 alkyl group, e.g. ethyl, n-propyl, tso-propyl, n-butyl, sec-butyl.

The C3–C6 alkenyl group is preferably a C3–C4 alkenyl group, e.g. 2-propenyl, 2-butenyl.

The C2–C6 acyl is preferably a C2–C4 acyl group, e.g. acetyl, propionyl, butyryl.

The quaternary ammonium group is preferably a trimethylammonium- or a N-methylpyrrolidinium- or a N-methylpiperidinium- group.

The $R^1$ is preferably hydrogen, 2-hydroxyethyl, 3-hydroxypropyl, 2-aminoethyl, 3-aminopropyl, 2-(1-pyrrolidinyl)ethyl, 3-(1-pyrrolidinyl)propyl.

The $OR^6$ group is preferably hydroxy, 2-aminoethoxy, 3-aminopropoxy, 2-dimethylaminoethory, 3-dimethylaminopropoxy, 3-amino-2-hydroxypropoxy, 2,3-diaminopropoxy, 2-(1-pyrrolidinyl)ethoxy, 3-(1-pyrrolidinyl)propoxy.

The $NR^7R^8$ group is preferably amino, methylamino, ethylamino, n-propylamino, dimethylamino, diethylamino, pyrro -lidinyl, morpholino, piperazinyl, 1-imidazolyl, 2-aminoethylamino, 3-aminopropylamino.

The $NR^9R^{10}$ group is preferably amino, methylarnino, ethylamino, n-propylamino, fso-propylamino, dimethylamino, pyrrolidinyl, morpholino, piperazinyl, 1-imidazolyl, 1-guanidino, 2-aminoethylamino, 3-aminopropylamino, 2-(1-pyrrolidinyl)ethylamino, 3-(1-pyrrolidinyl)propylamino, 3-amino-2-hydroxypropylamino, 3-(1-pyrrolidinyl)2-hydroxypropylamino, 2,3-diaminopropylamino, (2-(1-pyrrolidinyl)ethyl) methylarnino.

Preferred examples of specific compounds according to the present invention are:

17β-Phenyl-5α-androst-1-ene-3β,14β,17α-triol
17β-(4-Methoxyphenyl)-5α-androst-1-ene-3β,14β,17α-triol
17β-(3-Furyl)-5α-androst-1-ene-3β,14β,17α-triol
17β-Phenylandrosta-4,15-diene-3β,14β,17α-triol 3β-(2-(1-Pyrrolidinyl)ethoxy)-17β-phenylandrosta-4,15-diene-14β,17α-diol
17β-Phenylandrost-4-ene-3β,14β,17α-triol
3β-(2-(1-Pyrrolidinyl)ethoxy)-17β-phenylandrost-4-ene-14β,17α-diol
17-Phenyl-17α-(2-(1-pyrrolidinyl)ethoxy)androst-4-ene-3β,14β-diol
3β,17α-Bis (2-(1-pyrrolidinyl)ethoxy)-17β-phenylandrost-4-en-14β-ol
17β-(4-Methoxyphenyl)androsta-4,15-diene-3β,14β,17α-triol
3β-(2-(1-Pyrrolidinyl)ethoxy)-17β-(4-methoxyphenyl)androsta-4,15-diene-14β,17α-diol
17β-(4-Methoxyphenyl)androst-4-ene-3β,14β,17α-triol
3β-(2-(1-Pyrrolidinyl)ethoxy)-17β-(4-methoxyphenyl)androst-4-ene-14β,17α-diol
1762 -(4-Methoxyphenyl)-17α-(2-(1-pyrrolidinyl)ethoxy)androst-4-ene -3β,14β-diol
3β,17α-Bis(2-(1-pyrrolidinyl)ethoxy)-17β-(4-methoxyphenyl)androst-4-en-14β-ol
17β-(4-Chlorophenyl)androst-4-ene-3β,14β,17α-triol
1762 -(4-(N,N-Dimethylaminophenyl))androst-4-ene-3β,14β,17α-triol
17β-(4-Carboxyphenyl)androst-4-ene-3β,14β,17α-triol
17β-(2-Furyl)androst-4-ene-3β,-triol
3β-(2-(1-Pyrrolidinyl)ethoxy)-17β-(2-furyl)androst-4-ene-14β,17α-diol
17β-(2-Furyl)-17α-(2-(1-pyrrolidinyl)ethoxy)androst-4-ene-3β,14β-diol
3β,17α-Bis(2-(1-pyrrolidinyl)ethoxy)-17β-(2-furyl)androst-4-en-14β-ol
17β-(3-Furyl)androsta-4,15-diene-3β,14β,17α-triol
3β-(2-(1-Pyrrolidinyl)ethoxy)-17β-(3-furyl)androsta-4,15-diene-14β,17α-diol
17β-(3-Furyl)androst-4-ene-3β,14β,17α-triol
3β-(2-(1-Pyrrolidinyl)ethoxy)-17β-(3-furyl)androst-4-ene-14β,17α-diol
17β-(3-Furyl)-17α-(2-(1-pyrrolidinyl)ethoxy)androst-4-ene-3β,14β-diol
3β,17α-Bis(2-(1-pyrrolidinyl)ethoxy)-17β-(3-furyl)androst-4-en-14β-ol
17β-(3-Thienyl)androst-4-ene-3β,14β,17α-triol
3β-(2-(1-Pyrrolidinyl)ethoxy)-17β-(3-thienyl)androst-4-ene-14β,17α-diol
17β-(3-Thienyl)-17α-(2-(1-pyrrolidinyl)ethoxy)androst-4-ene-3β,14β-diol
3β,17α-Bis (2-(1-pyrrolidinyl)ethoxy)-17β-(3-thienyl)androst-4-en-14β-ol
17β-(2-Pyridyl)androst-4-ene-3β,14β,17α-triol
17β-(3-Pyridyl)androst-4-ene-3β,14β,17α-triol
17β-(4-Pyridyl)androst-4-ene-3β,14β,17α-triol
17β-(3-(1-Methylpyridinium))androst-4-ene-3β,14β,17α-triol iodide
17β-(2-Pyrimidinyl)androst-4-ene-3β,14β,17α-triol
17β-(4-Pyrimidinyl)androst-4-ene-3β,14β,17α-triol
17β-(4-Pyridazinyl)androst-4-ene-3β,14β,17α-triol
17β-(2-Imidazolyl)androst-4-ene-3β,14β,17α-triol
17β-(1,2-Dimethyl-5-imidazolyl)androst-4-ene-3β,14β,17α-triol
17β-(2-Thiazolyl)androst-4-ene-3β,14β,17α-triol
17β-(4-Isoxazolyl)androst-4-ene-3β,14β,17α-triol
17β-Phenylandrosta-5,15-diene-3β,14β,17α-triol
17β-Phenylandrost-5-ene-3β,14β,17α-triol
3β-(2-(1-Pyrrolidinyl)ethoxy)-17β-phenylandrost-5-ene-14β,17α-diol
17β-Phenyl-17α-(2-(1-pyrrolidinyl)ethoxy)androst-5-ene-3β,14β-diol
3β,17α-Bis(2-(1-pyrrolidinyl)ethoxy)-17β-phenylandrost-5-en-14β-ol
17β-(4-Methoxyphenyl)androst-5-ene-3β,14β,17α-triol
3β-(2-(1-Pyrrolidinyl)ethoxy)-17β-(4-methoxyphenyl)androst-5-ene- 14β,17α-diol
17β-(4-Methoxyphenyl)-17α-(2-(1-pyrrolidinyl)ethoxy)androst-5-ene-3β,14β-diol
3β,17α-Bis (2-(1-pyrrolidinyl)ethoxy)-17β-(4-methoxyphenyl)androst-5-en-14β-ol
17β-(4-Chlorophenyl)androst-5-ene-3β,14β,17α-triol
17β-(4-(N,N-Dimethylaminophenyl))androst-5-ene-3β,14β,17α-triol
17β-(4-Carboxyphenyl)androst-5-ene-3β,14β,17α-triol
17β-(2-Furyl)androst-5-ene-3β,14β,17α-triol
3β-(2-(1- Pyrrolidinyl)ethoxy)-17β-(2-furyl)androst-5-ene -14β,17α-diol
17β-(2-Furyl)-17α-(2-(1-pyrrolidinyl)ethoxy)androst-5-ene-3β,14β-diol
3β,17α-Bis(2-(1-pyrrolidinyl)ethoxy)-17β-(2-furyl)androst-5-en-14β-ol
17β-(3-Furyl)androsta-5,15-diene-3β,14β,17α-triol
3β-(2-(1-Pyrrolidinyl)ethoxy)-17β-(3-furyl)androsta-5,15-diene-14β,17α-diol
17β-(3-Furyl)androst-5-ene-3β,14β,17α-triol
3β-(2-(1-Pyrrolidinyl)ethoxy)-17β-(3-furyl)androst-5-ene-14β,17α-diol
17β-(3-Furyl)-17α-(2-(1-pyrrolidinyl)ethoxy)androst-5-ene-3β,14β-diol
3β,17α-Bis(2-(1-pyrrolidinyl)ethoxy)-17β-(3-furyl)androst-5-en-14β-ol
17β-(3-Thienyl)androst-5-ene-3β,14β,17α-triol
3β-(2-(1-Pyrrolidinyl)ethoxy)-17β-(3-thienyl)androst-5-ene-14β,17α-diol
17β-(3-Thienyl)-17α-(2-(1-pyrrolidinyl)ethoxy)androst-5-ene-3β,14β-diol
3β,17α-Bis(2-(1-pyrrolidinyl)ethoxy)-17β-(3-thienyl)androst-5-en-14β-ol
17β-(2-Pyridyl)androst-5-ene-3β,14β,17α-triol
17β-(3-Pyridyl)androst-5-ene-3β,14β,17α-triol
17β-(4-Pyridyl)androst-5-ene-3β,14β,17α-triol
17β-(3-(1-Methylpyridinium))androst-5-ene-3β,14β,17α-triol iodide
17β-(2-Pyrimidinyl)androst-5-ene-3β,14β,17α-triol
17β-(4-Pyrimidinyl)androst-5-ene-3β,14β,17α-triol
17β-(4-Pyridazinyl)androst-5-ene-3β,14β,17α-triol
17β-(2-Imidazolyl)androst-5-ene-3β,14β,17α-triol
17β-(1,2-Dimethyl-5 -imidazolyl)androst-5-ene-3β,14β,17α-triol
17β-(2-Thiazolyl)androst-5-ene-3β,14β,17α-triol
17β-(4-Isoxazolyl)androst-5-ene-3β,14β,17α-triol
17β-Phenylandrosta-4,6-diene-3β,14β,17α-triol
17β-(4-Methoxyphenyl)androsta-4,6-diene-3β,14β,17α-triol
17β-(3-Furyl)androsta-4,6-diene-3β,14β,17α-triol
17β-Phenyl-5α-androst-15-ene-3β,14β,17α-triol
3β-(2-(1-Pyrrolidinyl)ethoxy)-17β-phenyl-5α-androst-15-ene-14β,17α-diol
17β-Phenyl-5α-androstane-3β,14β,17α-triol
3β-(2-(1-Pyrrolidinyl)ethoxy)-17β-phenyl-5α-androstane-14β,17α-diol
17β-Phenyl-17α-(2-(1-pyrrolidinyl)ethoxy)-5α-androstane-3β,14β-diol
3β,17α-Bis(2-(1-pyrrolidinyl)ethoxy)-17β-phenyl-5α-androstan-14β-ol
17β-(4-Methoxyphenyl)-5α-androstane-3β,14β,17α-triol
3β-(2-(1-Pyrrolidinyl)ethoxy)-17β-(4-methoxyphenyl)-5α-androstane-14β,17α-diol 17β-(4-Methoxyphenyl)-17α-(2-(1-pyrrolidinyl)ethoxy)-5α-androstane-3β,14β-diol
3β,17α-Bis(2-(1-pyrrolidinyl)ethoxy)-17β-(4-methoxyphenyl)-5α-androstan-14β-ol
17β-(4-Chlorophenyl)-5α-androstane-3β,14β,17α-triol
17β-(4-(N,N-Dimethylaminophenyl))-5α-androstane-3β,14β,17α-triol
17β-(4-Carboxyphenyl)-5α-androstane-3β,14β,17α-triol
17β-(2-Furyl)-5α-androstane-3β,14β,17α-triol
3β-(2-(1-Pyrrolidinyl)ethoxy)-17β-(2-furyl)-5α-androstane-14β,17α-diol
17β-(2-Furyl)-17α-(2-(1-pyrrolidinyl)ethoxy)-5α-androstane-3β,14β-diol
3β,17α-Bis (2-(1-pyrrolidinyl)ethoxy)-17β-(2-furyl)-5α-androstan-14β-ol
17β-(3-Furyl)-5α-androst-15-ene-3β,14β,17α-triol
3β-(2-(1-Pyrrolidinyl)ethoxy)-17β-(3-furyl)-5α-androstane-14β,17α-diol
17β-(3-Furyl)-5α-androstane-3β,14β,17α-triol
3β-(2-(1-Pyrrolidinyl)ethoxy)-17β-(3-furyl)-5α-androstane-14β,17α-diol
17β-(3-Furyl)-17α-(2-(1-pyrrolidinyl)ethoxy)-5α-androstane-3β,14β-diol
3β,17α-Bis(2-(1-pyrrolidinyt)ethoxy)-17β-(3-furyl)-5α-androstan-14β-ol
17β-(3-Thienyl)-5α-androstane-3β,14β,17α-triol
3β-(2-(1-Pyrrolidinyl)ethoxy)-17β-(3-thienyl)-5α-androstane-14β,17α-diol
17β-(3-Thienyl)-17α-(2-(1-pyrrolidinyl)ethoxy)-5α-androstane-3β,14β,diol
3β,17α-Bis(2-(1-pyrrolidinyl)ethoxy)-17β-(3-thienyl)-5α-androstan-14β-ol
17β-(2-Pyridyl)-5α-androstane-3β,14β,17α-triol
17β-(3-Pyridyl)-5α-androstane-3β,14β,17α-triol
17β-(4-Pyridyl)-5α-androstane-3β,14β,17α-triol
17β-(3-(1-Methylpyridinium))-5α-androstame-3β,14β,17α-triol iodide
17β-(2-Pyridyl-N-oxide)-5α-androstane-3β,14β,17α-triol
17β-(3-Pyridyl-N-oxide)-5α-androstane-3β,14β,17α-triol
17β-(4-Pyridyl-N-oxide)-5α-androstane-3β,14β,17α-triol
17β-(2-Pyrimidinyl)-5α-androstane-3β,14β,17α-triol
17β-(4-Pyrimidinyl)-5α-androstane-3β,14β,17α-triol
17β-(4-Pyridazinyl)-5α-androstane-3β,14β,17α-triol
17β-(2-Imidazolyl)-5α-androstane-3β,14β,17α-triol
17β-(1,2-Dimethyl-5-imidazolyl)androst-5-ene-3β,14β,17α-triol
17β-(2-Thiazolyl)-5α-androstane-3β,14β,17α-triol
17β-(4-Isoxazolyl)-5α-androstane-3β,14β,17α-triol
17α-(3-Furyl)-5α-androstane-3β,14β,17β-triol and the corresponding 3β-(2-hydroxyethoxy), 3β-(3-hydroxypropoxy), 3β-(2,3-dihydroxypropoxy), 3β-(2-aminoethoxy), 3β-(3-aminopropoxy), 3β-(2-methylaminoethoxy), 3β-(3-methylaminopropoxy), 3β-(2-dimethylaminoethoxy), 3β-(3-dimethylaminopropoxy), 3β-(2-diethylaminoethoxy), 3β-(3-diethylaminopropoxy), 3β-(3-(1-pyrrolidinyl)propoxy), 3β-(2,3-diaminopropoxy), 3β-(2-(2-(1-pyrrolidinyl)ethoxy)ethoxy), 3β-(2-guanidinoethoxy), 3β-(3-guanidinopropoxy) of the 3β-(2-(1-pyrrolidinyl)ethoxy) derivatives;

and the corresponding 17α-(2-hydroxyethoxy), 17α-(3-hydroxypropoxy), 17α-(2-aminoethoxy), 17α-(3-aminopropoxy), 17α-(3-(1-pyrrolidinyl)propoxy) of the 17α-(2-(1-pyrrolidinyl)ethoxy) derivatives;

and the corresponding 3β,17α-bis(2-hydroxyethoxy), 3β,17α-bis(3-hydroxypropoxy), 3β,17α-bis(2-aminoethoxy), 3β,17α-bis(3-aminopropoxy), 3β,17α-bis(3-(1-pyrrolidinyl)propoxy) of the 3β,17α-bis(2-(1-pyrrolidinyl)ethoxy) derivatives;

and the corresponding 3-oxo and 3-guanidinoimino of the corresponding 3β-ol derivatives:

and the corresponding 3β-(2-aminoethylthio), 3β-(3-aminopropylthio), 3β-(2-(1-pyrrolidinyl)ethylthio), 3β-(3-(1-pyrrolidinyl)propylthio), 3β-(2-(2-(1-pyrrolidinyl)ethoxy)ethylthio) of the 3β-(2-(1-pyrrolidinyl)ethoxy) derivatives.

The invention furthermore provides a process for the preparation of compounds of general formula (I), wherein $=$ is a single or double bond, wherein Y, R and $R^1$ are as above defined, which comprises reacting aryl or heterocyclyl organometallics with compounds of formula (II)

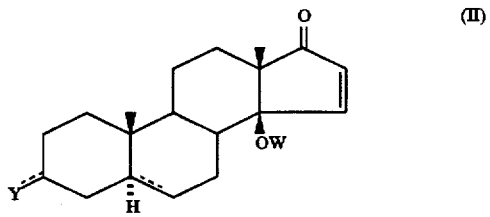

wherein $=$ is a single or double bond, wherein W is hydrogen or a protective group. Y is as above defined, with the proviso that Y is not a guanidinoimino and do not contain a guanidinoimino or a guanidino or an midino group, the hydroxy, mercapto, amino and oxo groups if any present in Y being protected, if necessary, with known methods, to give, if necessary, after removal of protective groups, ff any, present in Y and/or W, a compound of general formula (I), which can be converted into another compounds of general formula (I), by known methods such as conversion of hydroxy into mercapto function, alkylation of hydroxy or mercapto groups, oxydation of hydroxy or reduction of oxo functions, formation of guanidinoimino or guanidino or amidino groups from oxo or primary amino or cyano groups respectively, oxidation of a single bond to a double bond or migration of a double bond or reduction of a double bond to a single bond.

The nucleophilic reactions of aryl or heterocyclyl organometallics, wherein the metal is lithium, magnesium, cerium, zirconium or titanium, with compounds of formula (II) are carried out in an inert aprotic solvent, such as for example tetrahydrofuran, ethyl ether, dioxane, benzene, cyclohexane or a mixture of said solvents at a temperature ranging from −78° C. to room temperature.

Examples of conversions of compounds of general formula (I) into other compounds of formula (I) are the following.

Compounds (I) wherein an oxo function is present can be obtained by oxidation of the corresponding compounds (I) with a hydroxy function with e.g. $CrO_3$ in pyridine or tetrapropylammonium perruthenate and N-methylmorpholine-N-oxide in methylene chloride, at temperature ranging from 0° C. to room temperature.

Compounds (I) wherein Y is an α-hydroxy group can be obtained by reduction of the corresponding compounds (I) wherein Y is oxygen with complex hydrides, e.g. $NaBH_4$, $LiAlH_4$ or lithium tri-tert-butoxyaluminum hydride in methanol, tetrahydrofuran or ethyl ether, at temperature ranging from −78° C. to room temperature.

Compounds (I) wherein the 1–2 double bond is present can be obtained by halogenation of the corresponding 3-oxo or 3-enolacetates (I) with e.g. bromine and successive dehalogenation with bases e.g. lithium or calcium carbonate in polar solvents, e.g. DMF, DMA, pyridine or n-amyl alcohol at temperature ranging from 90° C. to the solvent reflux temperature, or by oxidation of enol silyl ether with DDQ in apolar solvent, e.g. benzene, toluene, chloroform, tetrahydrofuran, dioxane and mixture thereof at temperature ranging from room temperature to the solvent reflux temperature.

Compounds (I) wherein the functions 3-oxo $\Delta^4$ are present can be obtained by Oppenauer oxidation of the corresponding 3β-hydroxy $\Delta^5$ (I).

Compounds (I) wherein the functions 3-oxo $\Delta^{4,6}$ are present can be obtained by oxidation of the corresponding 3-oxo $\Delta^4$ (I) or their corresponding dienol ethers with e.g. DDQ or chloranil, in water/acetone or tert-butanol at temperature ranging from room temperature to the solvent reflux temperature.

Compounds (I) wherein the functions 3β-hydroxy $\Delta^4$ or $\Delta^{4,6}$ are present can be obtained by selective reduction of the corresponding 3-oxo $\Delta^4$ or $\Delta^{4,6}$ (I) with complex hydrides, e.g. LiAlH$_4$ or lithium tri-tert-butoxyaluminum hydride in tetrahydrofuran or ethyl ether, at temperature ranging from −78° C. to room temperature.

Compounds (I) wherein the 15–16 bond is a single bond can be obtained by selective hydrogenation of the compounds (I), wherein the 15–16 bond is a double bond, with e.g. hydrogen using palladium or platinum oxide as catalysts.

Compounds (I) wherein a guanidinoimino group is present can be obtained by condensation of the corresponding compounds (I) wherein an oxo function is present with e.g. aminoguanidine hydrogencarbonate in ethanol, methanol, acetonitrile, dioxane, tetrahydrofuran, water or a mixture of said solvents at temperature ranging from room temperature to the solvent reflux temperature.

Compounds (I) wherein Y is a β-mercapto group can be obtained by ammonolysis of the 3β-acetylthio derivatives (I) that are in turn obtained by reaction of the corresponding 3α-hydroxy derivatives (I) with e.g. thiolacetic acid in the presence of a dialkyl azodicarboxylate and triphenylphosphine, at temperature ranging from 0° C. to room temperature.

Compounds (I) wherein an ethereal or thioethereal function is present, e.g. wherein Y is OR$^2$ or SR$^2$ and wherein R$^1$ and/or R$^2$ are different from hydrogen, can be obtained from the corresponding compounds of formula (I), wherein Y is OR$^2$ or SR$^2$ and R$^1$ and/or R$^2$ are hydrogen, by reaction with alkylating compounds of formula (III) or (IV):

R$^1$-Z (III), R$^2$-Z (IV), wherein R$^1$ and R$^2$ are as above defined with the proviso that they are different from H and Z is an electron-withdrawing group, such as halogen, mesyloxy, or tosyloxy group, wieh confers electrophilic properties to the attached carbon atom. The reaction is carried out in an inert aprotic solvent, such as tetrahydrofuran, dioxane, dimethylformarnide, dimethylsulfoxide or in the R$^1$-Z and R$^2$-Z in the presence of a base, such as, e.g. sodium or potassium hydride, at a temperature ranging from 0° C. to reflux temperature of the reaction mixture.

Compounds (I) wherein a C(=NH)NH$_2$ is present can be obtained by reacting the corresponding compounds of formula (I) wherein a CN group is present with e.g. methylchtoroaluminum amide.

Compounds (I) wherein a guanidino group is present can be obtained by reacting the corresponding compounds of formula (I) wherein a primary amine is present with e.g. 1-amidino-3,5-dimethylpyrazole nitrate. All said transformations are examples of well established procedures described in Organic Chemistry (see for example: J. March "Advanced Organic Chemistry", J. Wiley & Sons, 1985; D. Barton and W. D. Ollis "Comprehensive Organic Chemistry", Pergamon Press, 1979: J. Fried and J. A. Edwards "Organic Reactions in Steroid Chemistry", Van Nostrand Reinhold Company, 1972) well known to those skilled in the art.

The compounds of formula (II), wherein Y is 3β-hydroxy, W is hydrogen and --- in position 5 is single or double bond are known compounds (G. Groszek et al., Bull Pol. Acad. Sci., Chem., 34, 1986, 313, U.S. Pat. No. 3,595,883).

The compounds of formula (II) wherein Y has the other meanings are obtained from the corresponding 3β-hydroxy (II) e.g. by conversion of hydroxy into mercapto function, alkylation of hydroxy or mercapto groups, oxydation of hydroxy or reduction of oxo functions with methods well known to those skilled in the art and described above.

The compounds of general formula (III) and (IV) are known compounds, generally commercially available or preparable from known compounds by known methods.

The compound 3β,14β,17α-trihydroxy-5β-card-20(22)-enolide (Ref. comp.) is known (N. Danieli, et al., Tetrah. Lett., 1962, 1281); this compound and its congeners are described as agents against cardiac insufficiency (DT Pat. 2614-046; F. G. Henderson and K. K. Chen, J. Med. Chem., 1965, 577), but do not show antihypertensive action.

We have found that the derivatives (I), prepared according to the invention, and their pharmaceutically acceptable salts have much reduced toxicity compared to the known 3β,14β,17α-trihydroxy-5β-card-20(22)-enolide and are useful agents for the treatment of cardiovascular disorders, such as heart failure and hypertension. Moreover said compounds (I) show affinity for the receptor site of the Na$^+$,K$^+$-ATPase and behave as partial agonists on the enzymatic activity of the Na$^+$,K$^+$-ATPase.

To test the affinity for the receptor site of the Na$^+$,K$^+$-ATPase and the inhibitory activity on the enzyme, the following tests were used: a) displacement of the specific $^3$H-ouabain binding from the Na$^+$,K$^+$-ATPase receptor purified according to Jorghensen (Jorghensen P., BBA, 1974, 356, 36) and Erdmann (Erdmann E. et al., Arzneim. Forsh., 1984, 34, 1314); b) inhibition of the activity of the purified Na$^+$,K$^+$-ATPase measured as % of hydrolysis of $^{32}$P-ATP in presence and in absence of the tested compound (Doucet A. et al., Am. J. Physiol, 1986, 251, F851).

The ability of these compounds to lower blood pressure was tested by using animal models with genetic arterial hypertension, in particular, spontaneous hypertensive rats of the Milan (MHS) (Bianchi G., Ferrari P., Barber B.The Milan Hypertensive strain. In Handbook of hypertension. Vol.4: Experimental and genetic models of hypertension. Ed. W. de jong-Elsevier Science Publishers B.V.,1984: 328–349).

The procedure adopted to test the antihypertensive activity of the compounds on the above mentioned model was the following: systolic blood pressure (SBP) and heart rate (HR) were measured by an indirect tail-cuff method in three-month old hypertensive rats (MHS) before beginrUng the treatment (basal values). The rats were then subdivided in two groups of at least 7 animals each, one receiving the compound the other, the control group, receiving only the vehicle. The compound, suspended in METHOCEL 0.5% (w/v), was administered daily by mouth, for ten days. SBP and HR were measured daily 6 and 24 hours after the treatment. At the end of the ten day treatment period, a washout period of at least two days was carried out, in order to check for how long the SBP was manrained low or the basal values were re-established.

The affinity and the inhibitory activity of some compounds and of the Ref. compound. in the two tests are shown in the following table:

|  | Binding $^3$H-Ouab. Displacement -log IC50 | Inhibitory Activity -log IC50 |
| --- | --- | --- |
| Comp. I - ab | 5.4 | 4.5 |
| Comp. I - ac | 5.2 | 4.1 |
| Comp. I - af | 5.1 | 4.1 |
| Comp. I - ah | 5.5 | 4.3 |
| Comp. I - ai | 5.3 | 4.4 |
| Comp. I - aj | 6.0 | 4.9 |
| Comp. I - al | 5.0 | 4.0 |
| Comp. I - an | 5.8 | 4.6 |
| Comp. I - ap | 5.1 | 4.0 |
| Comp. I - au | 5.3 | 4.5 |
| Comp. I - ay | 5.3 | 4.1 |
| Comp. I - bi | 5.5 | 4.4 |
| Comp. I - bj | 5.3 | 4.0 |
| Comp. I - bk | 5.1 | 4.2 |
| Comp. I - bl | 5.3 | 4.2 |
| Comp. I - bm | 5.0 | 4.0 |
| Comp. I - bn | 5.1 | 4.2 |
| Comp. I - bo | 5.0 | 4.0 |
| Comp. I - bp | 5.2 | 4.3 |
| Comp. I - bq | 5.3 | 4.1 |
| Comp. I - br | 5.8 | 4.6 |
| Comp. I - bs | 5.4 | 4.4 |
| Comp. I - bt | 5.5 | 4.3 |
| Comp. I - bu | 5.5 | 4.2 |
| Comp. I - bv | 5.4 | 4.1 |
| Comp. I - bw | 5.4 | 4.0 |
| Comp. I - by | 5.8 | 4.9 |
| Ref.comp. | 5.9 | 5.3 |

The activity of the Ref. compound and some new compound in lowering blood pressure in spontaneous hypertensive MHS rats is shown in the following table:

| SYSTOLIC BLOOD PRESSURE FALL IN SPONTANEOUS HYPERTENSIVE RATS (MHS) | | | |
| --- | --- | --- | --- |
| Compound | RATS | DOSE* mg/Kg/os | SBP mm Hg | HR beats/min. |
| Controls | 7 | METHOCEL | 172 +/− 2.0 | 328 +/− 8.6 |
| Comp. I - ae | 7 | 20 | 157 +/− 3.7 | 312 +/− 9.4 |
| Comp. I - ah | 7 | 20 | 154 +/− 4.1 | 315 +/− 10.1 |
| Comp. I - aj | 7 | 20 | 150 +/− 3.9 | 310 +/− 9.0 |
| Comp. I - bl | 7 | 20 | 156 +/− 3.5 | 318 +/− 9.5 |
| Ref. comp. | 7 | 20 | 174 +/− 2.1 | 340 +/− 10.2 |

*in METHOCEL 0.5% w/v

The following examples illustrate the invention without limiting it.

EXAMPLE 1

17β-Phenyl-5α-androst-1-ene-3β,14β,17α-triol (I-aa)

To a solution of 14β,17α-dihydroxy- 17β-phenyl-5α-androstan-3-one (I-az) (4.80 g) in 4.2 ml of dry triethylamine and 5 ml of dry dimethylformammide, under nitrogen atmosphere, 1.93 ml of chlorotrimethylsilane was added. The mixture was heated at 130° C. for 90 hrs, then, after cooling, it was diluited with 200 ml of ether and washed with 20 ml of a saturated solution of sodium hydrogen carbonate; the aqueous phase was extracted with diethyl ether (3×20 ml) and the combined organic phases were washed rapidly in turn with 25 ml of hydrochloric acid 0.5M, a saturated solution of sodium hydrogen carbonate (2×20 ml) and 20 ml of water. The organic layer was dried over sodium sulfate and evaporated to dryness under reduced pressure to give 3.32 g of the crude 3-trimethylsilyloxy-17β-phenyl-5α-androst-2-ene-14β, 17α-diol.

$^1$H-NMR (300 MHz, CDCl$_3$, ppm from TMS): 0.16 (9H, s); 0.70 (3H, s); 0.79 (3H, s); 2.68–2.79 (1H, m); 4.58–4.70 (1H, m); 7.22–7.38 (3H, m): 7.57–7.65 (2H, m).

To 3.32 g of 3-trimethylsilyloxy-17β-phenyl-5α-androst-2-ene-14β,17α-diol in 100 ml of dry benzene, under nitrogen atmosphere, a solution of 7.20 g of DDQ in 400 ml of dry benzene was added dropwise over 2.5 hrs. After 23 hrs, the mixture was partitioned between 100 ml of a saturated solution of sodium hydrogen carbonate and 400 ml of diethyl ether. The acqueous layer was extracted with diethyl ether (3×100 ml), the combined organic layers were dried over sodium sulfate and evaporated to dryness under reduced pressure to give 1.70 g of 14β,17α-dihydroxy-17β-phenyl-5α-androst-1-en-3-one as a white solid.

$^1$H-NMR (300 MHz, CDCl$_3$, ppm from TMS): 0.73 (3H, s); 0.98 (3H, s); 2.68–2.79 (1H, m); 5.92 (1H, d); 6.85 (1H, d); 7.22–7.38 (3H, m); 7.57–7.65 (2H, m).

To 1.7 g of 14β,17α-dihydroxy-17β-phenyl-5α-androst-1-en-3-one in 100 ml of dioxane/water 4/1 0.68 g of sodium borohydride were added, at room temperature. After one hr the organic solvent was evaporated and the aqueous phase was extracted with methylene chloride; the organic layer was dried over sodium sulfate and evaporated to dryness under reduced pressure. The residue was purified by flash-chromatography (SiO$_2$) using cyclohexane/ethyl acetate 80/20 as eluant to give 0.60 g of the title compound (I-aa) as a white solid.

$^1$H-NMR (300 MHz, CDCl$_3$, ppm from TMS): 0.85 (3H, s); 1.05 (3H, s); 2.68–2.79 (1H, m); 4.20 (1H, m); 4.71–5.02 (1H, m); 5.55–5.71 (1H, m); 7.22–7.38 (3H, m); 7.57–7.65 (2H, m).

EXAMPLE 2

17β-(3-Furyl)-5α-androst-1-ene-3β,14β,17α-triol (I-ab)

The title compound (I-ab) (0.04 g) was obtained as a white solid from 14β,17α-dihydroxy-17β-(3-furyl)-5α-androstan-3-one (I-b/) (4.8 g) using the same procedure described in Ex. 1.

$^1$H-NMR (300 MHz, CDCl$_3$, ppm from TMS): 0.85 (3H, s); 0.95 (3H, s); 4.20 (1H, bs); 5.92 (1H, d); 6.53 (1H, bs); 6.85 (1H, d); 7.35 (1H, bs); 7.42 (1H, bs).

EXAMPLE 3

17β-Phenylandrost-4-ene-3β,14β,17α-triol (I-ac)

To a solution of 1.90 g of 14β,17α-dihydroxy-17β-phenylandrost-4-en-3-one (I-af) in 10 ml of dry tetrahydrofuran at room temperature, under nitrogen atmosphere, a solution of 2.54 g of tri-tert-butoxyaluminum hydride in dry tetrahydrofuran was added dropwise. The mLxture was stirred for 20 hrs, then 30 ml of water were added. The aluminum salts were filtered on a celite cake and washed with methanol. The filtered solution was concentrated under reduced pressure and extracted with methylene chloride. The organic layer was dried over sodium sulfate and evaporated to dryness under reduced pressure; the residue was purified by flash-chromatography (SiO$_2$) using n-hexane/ethyl acetate 80/20 as eluant to give 1.80 g of the title compound (I-ac) as a white solid.

¹H-NMR (300 MHz, CDCl₃, ppm from TMS): 0.72 (3H, s); 1.03 (3H, s): 2.65–2.79 (1H, m); 4.14–4.26 (1H, m); 5.32 (1H, bs); 7.22–7.38 (3H, m); 7.57–7.65 (2H, m).

EXAMPLE 4

3β-(3-Hydroxypropoxy)-17β-phenylandrost-4-ene-14β,17α-diol (I-ad)

To a suspension of 0.12 g of NaH (60% dispersion in mineral oil) in 13 ml of dry tetrahydrofuran 0.38 g of 17β-phenylandrost-4-ene-3β,14β,17α-triol (I-ac) were added at room temperature, under nitrogen atmosphere and the resulting mixture was refluxed for half an hr; 0.40 g of allyl bromide were added and the reflux continued for half an hr. The mixture was quenched with water and the organic solvent was distilled under reduced pressure. The residue was extracted with ethyl acetate, the organic solution was dried over sodium sulfate and evaporated to dryness under reduced pressure. The residue was purified by flash-chromatography (SiO₂) using n-hexane/ethyl acetate 80/20 as eluant to give 0.25 g of 3β-(prop-2-enoxy)-17β-phenylandrost-4-ene-14β,17α-diol as a dense oil.

¹H-NMR (300 MHz, CDCl₃, ppm from TMS): 0.65 (3H, s); 1.03 (3H, s); 2.65–2.79 (1H, m); 3.67–3.77 (1H, m); 3.95 (2H, m); 5.15 (1H, m); 5.20–5.35 (2H, m); 5.87–6.02 (1H, m); 7.22–7.38 (3H, m); 7.57–7.65 (2H, m).

To a solution of 0.085 g of 9-borabicyclo[3.3.1]nonane in 190 ml of dry tetrahydrofuran, 0.25 g of 3β-(prop-2-enoxy)-17β-phenylandrost-4-ene-14β,17α-diol in 5 ml of tetrahydrofuran were added under nitrogen atmosphere, at room temperature. The solution was stirred for 6 hrs, then 0.5 ml of ethanol, 0.2 ml of sodium hydroxide 6N and 0.3 ml of hydrogen peroxide 30% were added. The mixture was stirred at 50° C. for one hr, quenched with a solution of 0.5 g of potassium carbonate in 10 ml of water and the organic solvent distilled under reduced pressure. The residue was extracted with methylene chloride, the organic solution was dried over sodium sulfate and evaporated to dryness under reduced pressure. The residue was purified by flash-chromatography (SiO₂) using n-hexane/ethyl acetate 70/30 as eluant to give 0.22 g of the title compound (I-ad) as a white amorphous solid.

¹H-NMR (300 MHz, CDCl₃, ppm from TMS): 0.65 (3H, s): 1.03 (3H, s); 2.65–2.79 (1H, m); 3.42–3.52 (2H, m); 3.61–3.77 (3H, m); 5.32 (1H, m); 7.22–7.38 (3H, m); 7.57–7.65 (2H, m).

EXAMPLE 5

3β-(3-Aminopropoxy)-17β-phenylandrost-4-ene-14β,17α-diol (I-ae)

A solution of 0.083 ml of diethyl azodicarboxytate was added dropwise, under nitrogen atmosphere, to a solution of 0.22 g of 3β-(3-hydroxypropoxy)-17β-phenylandrost-4-ene-14β,17α-diol (I-ad), 0.077 g of phthalimide and 0.15 g of triphenylphosphine in 2 ml of tetrahydrofuran at room temperature. After 2 hrs the solvent was removed under reduced pressure and the crude product was purified by flash-chromatography (SiO₂) using n-hexane/ethyl acetate 80/20 to give 0.20 g of 3β-(3-phthalimidopropoxy)-17β-phenylandrost-4-ene-14β,17α-diol as a white solid.

¹H-NMR (300 MHz, CDCl₃, ppm from TMS): 0.65 (3H, s); 0.97 (3H, s); 2.65–2.79 (1H, m); 3.38–3.5I (2H, m); 3.67–3.87 (3H, m); 5.32 (1H, m); 7.22–7.38 (3H, m); 7.57–7.77 (4H, m); 7.82–7.89 (2H, m).

To a solution of 0.15 g of 3β-(3-phthalimidopropoxy)-17β-phenylandrost-4-ene-14β,17α-diol in 20 ml of ethanol, 0.075 g of hydrazine hydrate were added at room temperature. The mixture was kept at reflux temperature for 4 hrs, then 5 ml of water were added and the ethanol distilled under reduced pressure. The residue was extracted with methylene chloride, the organic solution was washed with water, dried over sodium sulfate and evaporated under reduced pressure. The crude residue was purified by flash-chromatography (SiO₂) using methylene chloride/methanol 90/10 as eluant to give 0.080 g of the title compound (I-ae) as a white solid.

¹H-NMR (300 MHz, CDCl₃, ppm from TMS): 0.72 (3H, s); 0.97 (3H, s); 2.65–2.90 (3H, m); 3.42–3.51 (2H, m); 3.67–3.77 (1H, m); 5.32 (1H, m); 7.22–7.38 (3H, m); 7.57–7.65 (2H, m).

EXAMPLE 6

14β,17α-Dihydroxy-17β-phenylandrost-4-en-3-one (I-af)

A solution of 2.16 g of aluminum isopropoxide in 80 ml of dry toluene was added to a solution of 2.68 g of 17β-phenylandrost-5-ene-3β,14β,17α-triol (I-ap) in 100 ml of dry toluene e 38 ml of cyclohexanone. The resulting mixture was refluxed for 2 hrs, under nitrogen atmosphere, then the mixture was quenched with water and the organic solvent was distilled under reduced pressure. The residue was purified by flash-chromatography (SiO₂) using n-hexane/ethyl acetate 90/10 as eluant to give 2.2 g of the title compound (I-af) as a white sollet.

¹H-NMR (300 MHz, CDCl₃, ppm from TMS): 0.77 (3H, s); 1.18 (3H, s); 2.68–2.79 (1H, m); 5.77 (1H, bs); 7.22–7.38 (3H, m); 7.57–7.65 (2H, m).

EXAMPLE 7

3-Guanidinoimino-17β-phenylandrost-4-ene-14β, 17α-diol (I-ag)

The solution of 0.70 g of 14β,17α-dihydroxy-17β-phenylandrost-4-en-3-one (I-af) in 10 ml of ethanol was added to a solution of 0.52 g of aminoguanidine hydrogencarbonate and 38 ml of NaOH 0.1N. The resulting mixture was kept at reflux for 0.5 hrs, then the ethanol was evaporated. The precipitate was filtered, washed with water, then with diethyl ether and dried by heating at 60° C. under reduced pressure to give 0.70 g of the title compound (I-ag) as a white solid.

¹H-NMR (300 MHz, DMSO-d6, ppm from TMS): 0.52 (3H, s); 1.03 (3H, s); 3.57 (1H, bs); 4.55 (1H, bs); 5.03 (2H, m); 5.32 (1H, bs); 5.45 (2H, bs); 7.22–7.38 (3H, m); 7.57–7.65 (2H, m).

EXAMPLE 8

17β-(3-Furyl)androst-4-ene-3β,14β,17α-triol (I-ah)

To a solution of 2.0 g of 14β,17α-dihydroxy-17β-(3-furyl)androst-4-en-3-one (I-am) in 24 ml of dry tetrahydrofuran at −78° C., a solution of 4.5 g of tri-tert-butoxyaluminum hydride in dry tetrahydrofuran was added dropwise, under nitrogen atmosphere. The mixture was stirred for 20 hrs, the temperature was left to rise to 25° C., then 30 ml of water were added. The aluminum salts were filtered on a celite cake, washed with methanol; the filtered solution was concentrated under reduced pressure and extracted with methylene chloride. The organic layer was dried over sodium sulfate and evaporated to dryness under reduced pressure to give 1.80 g of the title compound (I-ah) as a white solid.

¹H-NMR (300 MHz, CDCl₃ ppm from TMS): 0.75 (3H, s); 1.05 (3H, s); 4.18 (1H, bs); 5.35 (1H, bs); 6.53 (1H, bs); 7.35 (1H, bs); 7.42 (1H, bs).

EXAMPLE 9

3β-(2-Hydroxyethoxy)-17β-(3-furyl)androst-4-ene-14β,17α-diol (I-ai)

To a suspension of 0.24 g of NaH (60 % dispersion in mineral oil) in 22 ml of dry tetrahydrofuran 0.74 g of 17β-(3-furyl)androst-4-ene-3β,14β,17α-triol (I-ah) were added at room temperature, under nitrogen atmosphere and the resulting mixture was refluxed for half an hr; 1.2 ml of bromoacetaldehyde diethylacetal were added and the suspension was kept at reflux temperature for half an hr, then 10 ml of water were added cautiously, and the tetrahydrofuran was distilled under reduced pressure. The residue was extracted with methylene chloride, the organic layer was dried over sodium sulfate and evaporated to dryness under reduced pressure. The crude product was purified by flash-chromatography (SiO₂) using n-hexane/ethyl acetate 80/20 as eluant t.o give 0.36 g of 3β-(2,2-diethoxyethoxy)-17β-(3-furyl)androst-4-ene-14β,17α-diol as a dense oil.

¹H-NMR (300 MHz, CDCl₃ ppm from TMS): 0.87 (3H, s); 1.07 (3H, s); 2.39–2.52 (1H, m); 3.43 (2H, m); 3.52–3.79 (5H, m); 4.61 (1H, t); 5.32 (1H, bs); 6.53 (1H, bs); 7.37 (1H, mbs); 7.42 (1H, bs).

A solution of 0.36 g of 3β-(2,2-diethoxyethoxy)-17β-(3-furyl)androst-4-ene-14β,17α-diol in 30 ml of dioxane and 22 ml of a saturated solution of tartaric acid was heated at 60° C. for 2 hrs under nitrogen atmosphere; 10 ml of water were then added and the residue was extracted with methylene chloride. The organic layer was washed with water, dried over sodium sulfate and evaporated to dryness under reduced pressure. The crude product was purified by flash-chromatography (SiO₂) using as eluant n-hexane/ethyl acetate 70/30 to give 0.24 g of 3β-formylmethoxy-17β-(3-furyl)androst-4-ene-14β,17α-diol as a white solid.

¹H-NMR (300 MHz, CDCl₃ ppm from TMS): 0.87 (3H, s); 1.07 (3H, s); 2.39–2.52 (1H, m); 3.64–3.77 (1H, m); 4.03 (2H, bs); 6.53 (1H, bs): 7.37 (1H, bs); 7.42 (1H, bs); 9.77 (1H, bs).

To a solution of 0.19 g of 3β-formylmethoxy-17β-(3-furyl)androst-4-ene-14β,17α-diol in 10 ml of methanol, 0.033 g of sodium borohydride were added slowly at 0° C. and after half an hr the temperature of the mixture was left to rise to 25 ° C. After 2 hrs 10 ml of water were added, the methanol was distilled under reduced pressure, and the mixture was extracted with methylene chloride; the organic layer was washed with water, dried over sodium sulfate and evaporated to dryness under reduced pressure. The crude product was purified by flash-chromatography (SiO₂) using n-hexane/ethyl acetate 80/20 as eluant to give 0.17 g of the title compound (I-ai) as a white solid.

¹H-NMR (300 MHz, CDCl₃ ppm from TMS): 0.77 (3H, s); 1.05 (3H, s); 2.39–2.52 (1H, m); 3.42–3.52 (2H, m); 3.61–3.77 (3H, m); 5.32 (1H, bs); 6.53 (1H, bs); 7:37 (1H, bs); 7.42 (1H, bs).

EXAMPLE 10

3β-(3-Aminopropoxy)-17β-(3-furyl)androst-4-ene-14β,17α-diol (I-aj)

The title compound (I-aj) (0.070 g) was obtained as a white solid from 17β-(3-furyl)androst-4-ene-3β,14β,17α-triol (I-ah) (0.90 g) using the sequence described in Ex. 4 and Ex.5.

¹H-NMR (300 MHz, CDCl₃ ppm from TMS): 0.87 (3H, s); 1.07 (3H, s); 2.39–2.52 (1H, m); 2.70–2.90 (2H, m); 3.42–3.51 (2H, m); 3.64–3.77 (1H, m); 5.32 (1H, bs); 6.53 (1H, bs); 7.37 (1H, bs); 7.42 (1H, bs).

EXAMPLE 11

3β,17α-Bis(3-hydroxypropoxy)-17β-(3-furyl)androst-4-en-14β-ol (I-ak)

To a solution of 1.20 g of 17β-(3-furyl)androst-4-ene-3β,14β,17α-triol (I-ah) in 100 ml of dry tetrahydrofuran, 2.52 g of sodium hydride (60% dispersion in mineral oil) were added under nitrogen atmosphere, at room temperature and the resulting mixture was stirred at reflux temperature for 6 hrs; 8.1 g of allyl bromide were added and the reflux continued for further 8 hrs. The mixture was quenched with water and the organic solvent was distilled under reduced pressure. The residue was extracted with ethyl acetate, the organic solution was dried over sodium sulfate and evaporated to dryness under reduced pressure. The residue was purified by flash-chromatography (SiO₂) using n-hexane/ethyl acetate 80/20 as eluant to give 1.10 g of 3β,17α-bis(prop-2-enoxy)-17β-(3-furyl)androst-4-en-14β-ol as a white solid.

¹H-NMR (300 MHz, CDCl₃ ppm from TMS): 0.93 (3H, s); 1.05 (3H, s); 3.67–3.80 (3H, m); 3.95 (2H, m); 5.10–5.18 (2H, m); 5.20–5.35 (3H, m); 5.83–6.05 (2H, m): 6.40(1H, bs); 7.38 (2H, m).

To a solution of 0.77 g of 9-borabicyclo[3.3.1]nonane in 70 ml of dry tetrahydrofuran, 1.0 g of 3β,17α-bis(prop-2-enoxy)-17β-(3-furyl)androst-4-en-14β-ol in 40 ml of tetrahydrofuran were added under nitrogen atmosphere, at room temperature. The solution was stirred for 6 hrs, then 3 ml of ethanol, 1 ml of sodium hydroxide 6N and 2 ml of hydrogen peroxide 30% were added. The mixture was stirred at 50° C. for one hr, a solution of 3 g of potassium carbonate in 80 ml of water were added and the organic solvent distilled under reduced pressure. The residue was extracted with methylene chloride, the organic solution was dried over sodium sulfate and evaporated to dryness under reduced pressure. The residue was purified by flash-chromatography (SiO₂) using n-hexane/ethyl acetate 70/30 as eluant to give 0.72 g of the title compound (I-ak) as a white amorphous solid.

¹H-NMR (300 MHz, CDCl₃ ppm from TMS): 0.93 (3H, s); 1.05 (3H, s); 3.10–3.30 (2H, m); 3.35–3.52 (2H, m); 3.56–3.77 (5H, m); 5.32 (1H, m); 6.40 (1H, bs); 7.38 (2H, m).

EXAMPLE 12

3β,17α-Bis(3-aminopropoxy)-17β-(3-furyl)androst-4-ene-14β,17α-diol (I-al)

A solution of 0.33 ml of diethyl azodicarboxylate was added dropwise, under nitrogen atmosphere, to a solution of 0.50 g of 3β,17α-bis(3-hydroxypropoxy)-17β-(3-furyl)androst-4-en-14β-ol (I-ak), 0.89 g of phthalimide and 0.31 g of triphenylphosphine in 4 ml of tetrahydrofuran at room temperature. After 2 hrs the solvent was removed under reduced pressure and the crude product was purified by flash-chromatography (SiO₂) using n-hexane/ethyl acetate 80/20 to give 0.31 g of 3β,17α-bis(3-phthalimidopropoxy)-17β-(3-furyl)androst-4-en-14β-ol as a white solid.

¹H-NMR (300 MHz, CDCl₃ ppm from TMS): 0.93 (3H, s); 0.97 (3H, s); 3.30–3.51 (4H, m); 3.53–3.62 (2H, m); 3.67–3.80 (1H, m); 3.76–3.87 (2H, m); 5.32 (1H, bs); 6.40 (1H, bs); 7.38 (2H, m); 7.68–7.77 (4H, m); 7.82–7.89 (4H, m).

To a solution of 0.30 g of 3β,17α-bis(3-phthalimidopropoxy)-17β-(3-furyl)androst-4-en-14β-ol in 35 ml of ethanol 1.30 g of hydrazine hydrate were added at room temperature: The mixture was kept at reflux for 4 hrs, then 20 ml of water were added and the ethanol distilled under reduced pressure. The residue was extracted with methylene chloride, the organic solution was washed with water, dried over sodium sulfate and evaporated to dryness under reduced pressure. The crude residue was purified by flash-chromatography (SiO$_2$) using methylene chloride/methanol 90/10 as eluant to give 0.15 g of the title compound (I-al) as a white solid.

$^1$H-NMR (300 MHz, CDCl$_3$ ppm from TMS): 0.93 (3H, s); 1.05 (3H, s); 2.80–2.95 (4H, m); 3.17–3.30 (2H, m); 3.42–3.55 (2H, m); 3.64–3.77 (1H, m); 5.32 (1H, bs); 6.40 (1H, bs); 7.38 (2H, m).

EXAMPLE 13

14β,17α-Dihydroxy-17β-(3-furyl)androst-4-en-3-one (I-am)

The title compound (I-am) (2.0 g) was obtained as a white solid from 17β-(3-furyl)androst-5-ene-3β,14β,17α-triol (I-at) (2.50 g) using the same procedure described in Ex. 6.

$^1$H-NMR (300 MHz, CDCl$_3$ ppm from TMS): 0.91 (3H, s); 1.21 (3H, s); 2.39–2.52 (1H, m); 5.77 (1H, bs); 6.53 (1H, bs); 7.37 (1H, m); 7.42 (1H, bs).

EXAMPLE 14

3-Guanidinoimino-17β-(3-furyl)androst-4-ene-14β,17α-diol (I-an)

The title compound (I-an) (0.35 g) was obtained as a white solid from 14β,17α-dihydroxy-17β-(3-furyl)androst-4-en-3-one (I-am) (0.33 g) using the same procedure described in Ex. 7.

$^1$H-NMR (300 MHz, DMSO-d6, ppm from TMS): 0.65 (3H, s); 0.93 (3H, s); 3.57 (1H, bs); 4.55 (1H, bs); 5.03 (2H, bs); 5.32 (1H, bs); 5.45 (2H, bs); 6.53 (1H, bs); 7.37 (1H, m); 7.42 (1H, bs).

EXAMPLE 15

17β-Phenylandrosta-5,15-diene-3β,14β,17α-triol (I-ao)

14.80 g of anhydrous CeCl$_3$ was suspended in 20 ml of dry tetrahydrofuran, under nitrogen atmosphere; the suspension was cooled to −78° C. then 29.6 ml of phenyllithium (solution 2M in cyclohexane-ether) were added and kept at the same temperature for 2 hrs, when 6.0 g of 3β,14β-dihydroxyandrosta-5,15-dien-17-one (G. Groszek et al., Bull. Pol. Acad. Sci. Chem., 34, 1986, 313) were added to the mixture. After one hr the reaction mixture was diluted with 150 ml of water, filtered through celite, and extracted with ethyl acetate: the combined extracts were dried over sodium sulfate and evaporated to dryness under reduced pressure. The crude product was purified by flash-chromatography (SiO$_2$) using ethyl acetate/cyclohexane 70/30 as eluant to give 4.30 g of the title compound (I-so) as a white solid.

$^1$H-NMR (300 MHz, CDCl$_3$ ppm from TMS): 0.86 (3H, s); 0.98 (3H, s); 3.49–3.62 (1H, m): 5.45 (1H, bs); 6.02 (1H, d); 6.48 (1H, d); 7.29–7.41 13H, m); 7.43–7.56 (2H, m).

EXAMPLE 16

17β-Phenylandrost-5-ene-3β,14β,17α-triol (I-ap)

To a solution of 5.0 g of 17β-phenylandrosta-5,15-diene-3β,14β,17α-triol (I-ao) in 370 ml of ethyl acetate 0.50 g of PtO$_2$ were added and the resulting mixture was shaken with hydrogen at room temperature. After 0.5 hrs, the mixture was filtered over celite and evaporated to give 4.7 g of the title compound (I-ap) as a white solid.

$^1$H-NMR (300 MHz, CDCl$_3$ ppm from TMS): 0.72 (3H, s); 0.98 (3H, s); 2.69–2.79 (1H, m); 3.49–3.62 (1H, bs); 5.40 (1H, bs); 7.22–7.38 (3H, m); 7.57–7.65 (2H, m).

EXAMPLE 17

3β-(3-Aminopropoxy)-17β-phenylandrost-5-ene-14β,17α-diol (I-aq)

The title compound (I-aq) (0.31 g) was obtained as a light yellow solid from 17β-phenylandrost-5-ene-3β,14β,17α-triol (I-ap) (1.20 g), using the sequence described in Ex. 4 and Ex. 5.

$^1$H-NMR (300 MHz, CDCl$_3$ ppm from TMS): 0.72 (3H, s); 0.98 (3H, s); 2.69–2.90 (3H, m); 3.12–3.26 (1H, bs); 3.42–3.51 (2H, m); 5.40 (1H, bs); 7.22–7.38 (3H, m); 7.57–7.65 (2H, m).

EXAMPLE 18

14β,17α-Dihydroxy-17β-phenylandrost-5-en-3-one (I-ar)

To a solution of 1.5 g of 17β-phenylandrost-5-ene-3β,14β,17α-triol (I-ap) in 25 ml of methylene chloride, 0.60 g of 4-methylmorpholine N-oxide, 0.075 g of tetrapropylammonium perruthenate and 1.5 g of powdered 4 Å molecular sieves were added at room temperature. After 4 hrs the solvent was evaporated to dryness under reduced pressure and the crude product purified by flash-chromatography (SiO$_2$) using n-hexane/ethyl acetate 70/30 as eluant to give 1.35 g of the title compound (I-ar) as a white solid.

$^1$H-NMR (300 MHz, CDCl$_3$ ppm from TMS); 0.72 (3H, s); 1.11 (3H, s); 2.68–2.79 (1H, m); 5.40 (1H, bs); 7.22–7.38 (3H, m); 7.57–7.65 (2H, m).

EXAMPLE 19

3-Guanidinoimino-17β-phenylandrost-5-ene-14β,17α-diol (I-as)

The title compound (I-as) (0.18 g) was obtained as a light yellow solid from 14β,17α-dihydroxy-17β-phenylandrost-5-en-3-one (I-ar) (0.24 g) using the same procedure described in Ex. 7.

$^1$H-NMR (300 MHz, DMSO-d6, ppm from TMS): 0.52 (3H, s); 1.15 (3H, s); 3.57 (1H, bs); 4.55 (1H, bs); 5.03 (2H, bs); 5.40–5.47 (3H, bs); 7.22–7.38 (3H, m); 7.57–7.65 (2H, m).

EXAMPLE 20

17β-(3-Furyl)androst-5-ene-3β,14β,17α-triol (I-at)

17β-(3-Furyl)androsta-5,15-diene-3β,14β,17α-triol (4.0 g), obtained from 3-furyllithium and 3β,14β-dihydroxyandrosta-5,15-dien-17-one (G.Groszek et al., Bull. Pol. Acad. Sci., Chem., 34, 1986, 313) as described in Ex. 15, was reduced with Pd/BaSO$_4$ as described in Ex. 16, to give the title compound (I-at) (2.9 g) as a white solid.

$^1$H-NMR (300 MHz, CDCl$_3$ ppm from TMS): 0.86 (3H, s); 0.97 (3H, s); 2.39–2.52 (1H, m); 3.49–3.62 (1H, m); 5.45 (1H, bs); 6.53 (1H, bs); 7.35 (1H, bs); 7.42 (1H, bs).

EXAMPLE 21

17β-Phenylandrosta-4,6-diene-3β,14β,17α-triol (I-au)

The title compound (I-au) (0.36 g) was obtained as a white solid from 14β,17α-dihydroxy-17β-phenylandrosta- 4,6-dien-3-one (I-av) (0.80 g) using the same procedure described in Ex. 3.

¹H-NMR (300 MHz, CDCl₃, ppm from TMS): 0.77 (3H, s); 1.18 (3H, s); 4.30 (1H, m); 5.45 (1H, s); 5.65 (1H, d); 5.91 (1H, dd); 7.22–7.38 (3H, m); 7.51–7.65 (2H, m).

EXAMPLE 22

14β,17α-Dihydroxy-17β-phenylandrosta-4,6-dien-3-one (I-av)

To a solution of 2.0 g of 14β,17α-dihydroxy-17β-phenylandrost-4-en-3-one (I-af) in 20 ml of tert-butanol, 2.58 g of chloranil was added. The solution was heated at reflux temperature for 5 hrs and then was evaporated under reduced pressure. The residue was extracted with methylene chloride, the organic layer was washed with a solution of NaOH 10% and water; then it was dried over sodium sulfate and evaporated to dryness under reduced pressure to give 0.80 g of the title compound (I-av) as a xvhite solid.

¹H-NMR (300 MHz, CDCl₃, ppm from TMS): 0.77 (3H, s); 1.18 (3H, s); 2.68–2.79 (1H, m); 5.71 (1H, s); 6.32 (2H, bs); 7.22–7.38 (3H, m); 7.51–7.65 (2H, m).

EXAMPLE 23

17β-Phenyl-5α-androst-15-ene-3β,14β,17α-triol (I-aw)

The title compound (I-aw) (3.50 g) was obtained as a white solid from 3β,14β-dihydroxy-5α-androst-15-en-17-one (U.S. Pat. No. 3,595,883) (4.0 g) using the same procedure described in Ex. 15.

¹H-NMR (300 MHz, CDCl₃ ppm from TMS): 0.79 (3H, s); 0.86(3H, s); 3.57–3.68 (1H, m); 6.02 (1H, d); 6.48 (1H, d); 7.29–7.41 (3H, m); 7.43–7.56 (2H, m).

EXAMPLE 24

3β-(3-Aminopropoxy)-17β-phenyl-5α-androst-15-ene-14β,17α-diol (I-ax)

The title compound (I-ax) (0.28 g) was obtained as a white solid from 17β-phenyl-5α-androst-15-ene-3β,14β,17α-triol (I-aw) (0.91 g) using the sequence described in Ex. 4 and Ex. 5.

¹H-NMR (300 MHz, CDCl₃ ppm from TMS): 0.79 (3H, s); 0.86 (3H, s); 2.68–2.70 (3H, m); 3.12–3.22 (1H, m); 3.42–3.51 (2H, m); 6.02 (1H, d); 6.48 (1H, d); 7.29–7.41 (3H, m); 7.43–7.56 (2H, m).

EXAMPLE 25

17β-Phenyl-5α-androstane-3β,14β,17α-triol (I-ay)

The title compound (I-ay) (0.88 g) was obtained as a white solid from 17β-phenyl-5α-androst-15-ene-3β,14β,17α-triol (I-aw) (0.95 g) using the same procedure described in Ex. 16.

¹H-NMR (300 MHz, CDCl₃ ppm from TMS): 0.70 (3H, s); 0.79 (3H, s); 2.68–2.79 (1H, m); 3.57–3.68 (1H, m); 7.22–7.38 (3H, m); 7.57–7.65 (2H, m).

EXAMPLE 26

14β,17α-Dihydroxy-17β-phenyl-5α-androstan-3-one (I-az)

The title compound (I-az) (0.50 g) was obtained as a white solid from 17β-phenyl-5α-androstane-3β,14β,17α-trioi (I-ay) (0.55 g) using the same procedure described in Ex. 18.

¹H-NMR (300 MHz, CDCl₃ ppm from TMS): 0.73 (3H, s); 0.98 (3H, s); 2.68–2.79 (1H, m); 7.22–7.38 (3H, m); 7.57–7.65 (2H, bs).

EXAMPLE 27

3β-(3-Aminopropoxy)-17β-phenyl-5α-androstane-14β,17α-diol (I-ba)

The tot;e compound (I-ba) (0.15 g) was obtained as a white solid from 17β-phenyl-5α-androstane-3β,14β,17α-triol (I-ay) (0.60 g) using the sequence described in Ex. 4 and Ex. 5.

¹H-NMR (300 MHz, CDCl₃ ppm from TMS): 0.70 (3H, s); 0.79 (3H, s); 2.68–2.90 (3H, m); 3.12–3.51 (3H, m); 7.22–7.38 (3H, m); 7.57–7.65 (2H, m).

EXAMPLE 28

17β-Phenyl-17α-(3-aminopropoxy)-5α-androstane-3β,14β-diol (I-bb)

A solution of 0.164 ml of diethyl azodicarboxylate was added dropwise, under nitrogen atmosphere, to a solution of 0.50 g of 3β-(tert-butyldimethylsilyloxy)-17β-phenyl-17α-(3-hydroxypropoxy)-5α-androstan-14β-ol, obtained as intermediate in Ex. 29, 0.15 g of phthalimide and 0.26 g of triphenylphosphine in 4 ml of tetrahydrofuran at room temperature. After 2 hrs the solvent was removed under reduced pressure and the crude product was purified by flash-chromatography (SiO₂) using n-hexane/ethyl acetate 80/20 to give 0.45 g of 3β-(tert-butyldimethylsilyloxy)-17β-phenyl-17α-(3-phthalimidopropoxy)-5α-androstan-14β-ol as a white solid.

¹H-NMR (300 MHz, CDCl₃ ppm from TMS): 0.03 (6H, s); 0.76 (3H, s); 0.79 (3H, s); 0.91 (9H, s); 3.30–3.51 (2H, m); 3.53–3.77 (3H, m); 7.22–7.38 (3H, m); 7.57–7.77 (4H, m); 7.82–7.89 (2H, m).

To a solution of 0.45 g of 3β-(tert-butyldimethylsilyloxy)-17β-phenyl-17α-(3-phthalimidopropoxy)-5α-androstan-14β-ol in 70 ml of ethanol, 0.18 g of hydrazine hydrate were added at room temperature. The mixture was kept at reflux temperature for 4 hrs, then 12 ml of water xvere added and the ethanol distilled under reduced pressure. The residue was extracted with methylene chloride, the organic solution was washed with water, dried over sodium sulfate and evaporated to dryness under reduced pressure. The crude residue was purified by flash-chromatography (SiO₂) using methylene chloride/methanol 90/10 as eluant to give 0.30 g of 3β-(tert-butyldimethylsilyloxy)-17β-phenyl-17α-(3-aminopropoxy)-5α-androstan-14β-ol as a white solid.

¹H-NMR (300 MHz, CDCl₃ ppm from TMS): 0.03 (6H, s); 0.76 (3H, s); 0.79 (3H, s); 0.91 (9H, s); 2.75–2.85 (2H, m); 3.17–3.30 (2H, m); 3.57–3.68 (1H, m); 7.22–7.38 (3H, m); 7.57–7.65 (2H, m).

To a solution of 0.30 g of 3β-(tert-butyldimethylsilyloxy)-17β-phenyl-17α-(3-aminopropoxy)-5α-androstan-14β-ol in 10 ml of tetrahydrofuran, 0.76 g of tetrabutylammonium fluoride trihydrate were added. The resulting mixture was kept at reflux for 20 hrs, then 20 ml of water were added and the tetrahydrofuran was distilled at reduced pressure. The residue was extracted with methylene chloride, the organic layer was dried over sodium sulfate and evaporated to dryness. The crude product was purified by flash-chromatography (SiO₂) using methylene chloride/methanol 90/10 as eluant to give 0.20 g of the title compound (I-bb) as a white solid.

¹H-NMR (300 MHz, CDCl₃ ppm from TMS): 0.76 (3H, s); 0.79 (3H, s); 2.75–2.85 (2H, m); 3.17–3.30 (2H, m); 3.57–3.68 (1H, m); 7.22–7.38 (3H, m); 7.57–7.65 (2H, m).

EXAMPLE 29

17β-Phenyl-17α-(3-hydroxypropoxy)-5α-androstane-3β,14β-diol (I-be)

To a solution of 2.9 g of tert-butyldimethylsilylchloride and 2.60 g of imidazole in 9 ml of dry dimethylformamide, 1.51 g of 17β-phenyl-5α-androstane-3β,14β,17α-triol (I-ay) were added, under nitrogen atmosphere, at room temperature. The resulting mixture was stirred for 6 hrs, then was diluted with water and extracted with ethyl acetate; the combined extracts were dried over sodium sulfate and evaporated to dryness under reduced pressure. The crude product was purified by flash-chromatography ($SiO_2$) using cyclohexane/ethyl acetate 95/5 as eluant to give 1.46 g of 3β-(tert-butyldimethylsilyloxy)-17β-phenyl-5α-androstane-14β,17α-diol as a white solid.

$^1$H-NMR (300 MHz, $CDCl_3$ ppm from TMS): 0.03 (6H, s); 0.70 (3H, s); 0.79 (3H, s); 0.91 (9H, s); 2.68–2.79 (1H, m); 3.52–3.63 (1H, m); 7.22–7.38 (3H, m): 7.57–7.65 (2H, m).

To a suspension of 1.2 g of NaH (60% dispersion in mineral oil) in 50 ml of dry tetrahydrofuran 0.80 g of 3β-(tert-butyldimethylsilyloxy)-17β-phenyl-5α-androstane-14β,17α-diol were added at room temperature, under nitrogen atmosphere and the resulting mixture was refluxed for half an hr; 3.84 g of allyl bromide were then added and the reflux continued for half an hr. The mixture was quenched with water and the organic solvent was distilled under reduced pressure. The residue was extracted with ethyl acetate, the organic solution was dried over sodium sulfate and evaporated to dryness under reduced pressure. The residue was purified by flash-chromatography ($SiO_2$) using n-hexane/ethyl acetate 80/20 as eluant to give 0.71 g of 3β-(tert-butyldimethylsilyloxy)-17β-phenyl-17α-(prop-2-enoxy)-5α-androstan-14β-ol as a white solid.

$^1$H-NMR (300 MHz, $CDCl_3$ ppm from TMS): 0.03 (6H, s); 0.76 (3H, s); 0.79 (3H, s); 0.91 (9H, s); 3.57–3.68 (1H, m); 3.67–3.80 (2H, m); 5.10–5.35 (2H, m); 5.83–6.05 (1H, m); 7.22–7.38 (3H, m); 7.57–7.65 (2H, m).

To a solution of 0.21 g of 9-borabicyclo[3.3.1]nonane in 450 ml of dry tetrahydrofuran, 0.60 g of 3β-(tert-butyldimethylsilyloxy)-17β-phenyl-17α-(prop-2-enoxy)-5α-androstan-14β-ol in 15 ml of tetrahydrofuran were added under nitrogen atmosphere, at room temperature. The solution was stirred for 6 hrs, then 1 ml of ethanol, 0.3 ml of sodium hydroxide 6N and 0.6 ml of hydrogen peroxide 30% were added. The mixture was stirred at 50° C. for one hr, quenched with a solution of 1.0 g of potassium carbonate in 20 ml of water and the organic solvent distilled under reduced pressure. The residue was extracted with methylene chloride, the organic solution was dried over sodium sulfate and evaporated to dryness under reduced pressure. The residue was purified by flash-chromatography ($SiO_2$) using n-hexane/ethyl acetate 70/30 as eluant to give 0.50 g of 3β-(tert-butyldimethylsilyloxy)-17β-phenyl-17α-(3-hydroxypropoxy)-5α-androstan-14β-ol as a white amorphous solid.

$^1$H-NMR (300 MHz, $CDCl_3$ ppm from TMS): 0.03 (6H, s): 0.76 (3H, s); 0.79 (3H, s); 0.91 (9H, s); 3.10–3.30 (2H, m); 3.56–3.77 (3H, m); 7.22–7.38 (3H, m); 7.57–7.65 (2H, m).

The title compound (I-bc) 0.12 g was obtained as a white amorphous solid from 0.50 g of 3β-(tert-butyldimethylsilyloxy)-17β-phenyl-17α(3-hydroxypropoxy)-5α-androstan-14β-ol following the procedure of desilylation described in Ex. 28.

$^1$H-NMR (300 MHz, $CDCl_3$ ppm from TMS): 0.76 (3H, s); 0.79 (3H, s); 3.10–3.30 (2H, m); 3.56–3.77 (3H, m); 7.22–7.38 (3H, m); 7.57–7.65 (2H, m).

EXAMPLE 30

3β,17α-Bis(3-aminopropoxy)-17β-phenyl-5α-androstan-14β-ol (I-bd)

The title compound (I-bd) (0.040 g) was obtained as a white solid from 17β-phenyl-5α-androstane-3β,14β,17α-triol (I-ay) (0.30 g) using the sequence described in Ex. 11 and Ex. 12.

$^1$H-NMR (300 MHz, $CDCl_3$ ppm from TMS): 0.76 (3H, s); 0.79 (3H, s); 2.80–2.95 (4H, m); 3.17–3.30 (2H, m); 3.42–3.55 (2H, m); 3.64–3.77 (1H, m); 7.22–7.38 (3H, m); 7.57–7.65 (2H, m).

EXAMPLE 31

17β-(3-Furyl)-5α-androstane-3β,14β,17α-triol (I-be)

The title compound (I-be) (1.70 g) was obtained as a white solid, using the same procedure described in Ex. 20, from 17β-(3-furyl)-5α-androst-15-ene-3β,14β,17α-triol (2.50 g), obtained from 3-furyllithium and 3β,14β-dihydroxy-5α-androst-15-en-17-one (U.S. Pat. No. 3,595,883) as described in Ex. 15.

$^1$H-NMR (300 MHz, $CDCl_3$ ppm from TMS): 0.79 (3H, s); 0.85 (3H, s); 2.39–2.52 (1H, m); 3.57–3.68 (1H, m); 6.53 (1H, bs); 7.37 (1H, bs); 7.42 (1H, bs).

EXAMPLE 32

14β,17α-Dihydroxy-17β-(3-furyl)-5α-androstan-3-one (I-bf)

The title compound (I-bf) (0.80 g) was obtained as amorphous solid from 17β-(3-furyl)-5α-androstane-3β,14β,17α-triol (I-be) (0.92 g) using the same procedure described in Ex. 18.

$^1$H-NMR (300 MHz, $CDCl_3$ ppm from TMS): 0.87 (3H, s); 0.98 (3H, s); 2.39–2.52 (1H, m); 6.53 (1H, bs); 7.37 (1H, bs); 7.42 (1H, bs).

EXAMPLE 33

3-Guanidinoimino-17β-(3-furyl)-5α-androstane-14β,17α-diol (I-bg)

The title compound (I-bg) (0.17 g) was obtained as a light yellow solid from 14β,17α-dihydroxy-17β-(3-furyl)-5α-androstan-3-one (I-bf) (0.20 g) using the same procedure described in Ex. 7.

$^1$H-NMR (300 MHz, DMSO-d6, ppm from TMS): 0.64 (3H, s); 1.03 (3H, s); 3.57 (1H, bs); 4.55 (1H, bs); 5.03 (2H, bs); 5.45 (2H, bs); 6.53 (1H, bs); 7.37 (1H, bs); 7.42(1H, bs).

EXAMPLE 34

17β-(4-Methoxyphenyl)androst-5-ene-3β,14β,17α-triol (I-bh)

To a solution of 24.80 ml of 4-bromoanisole in 200 ml of dry ether, at −30° C., under nitrogen atmosphere, 110 ml of butyllithium (solution 1.6M in hexane) were added. After 24 hrs the resulting mixture was added to a solution of 4.0 g of 3β-hydroxy-14β-ethoxymethoxyandrosta-5,15-dien-17-one (II-a, Prep. 1) in 150 ml of dry tetrahydrofuran and the suspension was kept stirring at the same temperature for one hr. The reaction mixture was diluted with 150 ml of water and extracted with ethyl acetate; the combined organic layers were dried over sodium sulfate and evaporated to dryness under reduced pressure. The crude product was purified by flash-chromatography (SiO$_2$) using cyclohexane/ethyl acetate 70/30 as eluant to give 4.20 g of 17β-(4-methoxyphenyl)-14β-ethoxymethoxyandrosta-5,15-diene-3β,17α-diol as a white solid.

$^1$H-NMR (300 MHz, CDCl$_3$, ppm from TMS): 0.80 (3H, s); 0.98 (3H, s); 3.40–3.65 (3H, m); 3.80 (3H, s); 4.40 (1H, d); 4.50 (1H, d); 5.40 (1H, bs); 5.95 (1H, d); 6.45 (1H, d); 6.85 (2H, d); 7.38 (2H, d).

To a solution of 4.16 g of 17β-(4-methoxyphenyl)-14β-ethoxymethoxyandrosta-5,15-diene-3β,17α-diol in 120 ml of ethyl acetate, 0.46 g of PtO$_2$ were added. The resulting mixture was shaken with hydrogen at room temperature. After half an hr the resulting mixture was filtered over celite and evaporated to give 3.68 g of the 17β-(4-methoxyphenyl)-14β-ethoxymethoxyandrost-5-ene-3β,17α-diol as a white solid.

$^1$H-NMR (300 MHz, CDCl$_3$, ppm from TMS): 0.70 (3H, s); 0.98 (3H, s); 2.35 (1H, m); 2.71 (1H, m); 3.20–3.65 (3H, m); 3.80 (3H, s); 4.0 (1H, d); 4.60 (1H, d); 5.40 (1H, bs); 6.85 (2H, m); 7.40 (2H, d).

160 ml of a solution of toluene-4-sulfonic acid in methanol/water 9/1 (pH=2.87) were added to 3.68 g of 17β-(4-methoxyphenyl)-14β-ethoxymethoxy-androst-5-ene-3β,17α-diol. After 18 hr at room temperature, 100 ml of a saturated solution of sodium hydrogen carbonate were added and the reaction mixture was extracted with ethyl acetate: the combined organic layers were washed with water, dried over sodium sulfate and evaporated to dryness under reduced pressure. The crude product was purified by flash-chromatography (SiO$_2$) using cyctohexane/ethyl acetate 60/40 as eluant to give 0.72 g of the title compound (I-bh) as a white solid.

$^1$H-NMR (300 MHz, CDCl$_3$, ppm from TMS): 0.70 (3H, s); 0.98 (3H, s); 2.19 (1H, m); 2.35 (1H, m); 2.70 (1H, m); 3.49–3.65 (1H, m); 3.80 (3H, s); 5.40 (1H, bs); 6.85 (2H, d); 7.50 (2H, d).

EXAMPLE 35

17β-(4-Methoxyphenyl)androst-4-ene-3β,14β,17α-triol (I-bi)

The title compound (I-bi) (0.75 g) was obtained as a white solid from 17β-(4-methoxyphenyl)androst-5-ene-3β,14β,17α-trlol (I-bh) (1.1 g) according to the sequence described in Ex. 6 and Ex. 8.

$^1$H-NMR (300 MHz, CDCl$_3$, ppm from TMS): 0.72 (3H, s); 1.03 (3H, s); 2.19 (1H, m); 2.35 (1H, m); 2.70 (1H, m); 3.80 (3H, s); 4.14–4.26 (1H, m); 5.32 (1H, bs); 6.85 (2H, d); 7.50 (2H, d).

EXAMPLE 36

17β-(4-Chlorophenyl)androst-5-ene-3β,14β,17α-triol (I-bi)

The title compound (I-bj) (2 g) was obtained as a white solid from 3β-hydroxy- 14β-ethoxymethoxyandrosta-5,15-dien-17-one (II-a, Prep. 1) (2.15 g) and the organometallic derivative obtained from 4-bromochlorobenzene as described in Ex. 34.

$^1$H-NMR (300 MHz, CDCl$_3$, ppm from TMS): 0.75 (3H, s); 0.98 (3H, s); 2.19 (1H, m); 2.39 (1H, m); 2.70 (1H, m); 3.49–3.62 (1H, m); 5.40 (1H, bs); 7.15–7.48 (4H, m).

EXAMPLE 37

17β-(3-Thienyl)-5α-androstane-3β,14β,17α-triol (I-bk)

The title compound (I-bk) (1.9 g) was obtained as a white solid from 3β-hydroxy-14β-ethorymethoxy-5α-androst-15-en-17-one (II-b, Prep. 2) (5.0 g) and 3-bromothiophene as described in Ex. 34, but the reduction of the Δ$^{15}$ was done shaking the reaction with hydrogen for a week and the PrO$_2$ was added every day. The deprotection of the 17β-(3-thienyl)-14β-ethoxymethoxy-5α-androstane-3β,17α-diol was conducted in dioxane and a solution of HCl 10$^{-2}$M was added until pH 2.6/3 was reached.

$^1$H-NMR (300 MHz, CDCl$_3$, ppm from TMS): 0.80 (3H, s); 0.83 (3H, s); 2.69 (1H, m); 3.57–3.68 (1H, m); 7.12 (1H, m); 7.21 (1H, m); 7. 35 (1H, m).

EXAMPLE 38

17β-(3-Pyridyl)-5α-androstane-3β,14β,17α-triol (I-bl)

The title compound (I-bl) (1.65 g) was obtained as a white solid from 3β-hydroxy-14β-ethoxymethoxy-5α-androst-15-en-17-one (II-b, Prep. 2) (2.50 g) and 3-bromopyridine as described in Ex. 34.

$^1$H-NMR (300 MHz, CDCl$_3$ ppm from TMS): 0.80 (3H, s); 0.83 (3H, s); 2.68 (1H, m); 3.57–3.68 (1H, m); 7.21 (1H, m); 7.81 (1H, m); 8.48 (1H, m); 8.68 (1H, m).

EXAMPLE 39

17β-(3-Pyridyl-N-oxide)-5α-androstane-3β,14β,17α-triol (I-bm)

A solution of 0.35 g of 17β-(3-pyridyl)-5α-androstane-3β,14β,17α-triol (I-bl) in 15 ml of chloroform was treated with 0.30 g of m-chloroperbenzoic acid at room temperature for 24 hrs. The mixture was then treated with aqueous sodium hydrogen carbonate and extracted with chloroform. The organic phase was dried over sodium sulfate and evaporated to dryness under reduced pressure. The crude product was purified by flash-chromatography (SiO$_2$) using chloroform/methanol/aqueous ammonia 78/20/2 as eluant to give 0.15 g of the title compound (I-bin), as a white solid.

$^1$H-NMR (300 MHz, CDCl$_3$, ppm from TMS): 0.80 (3H, s); 0.83 (3H, s); 2.68 (1H, m); 3.57–3.68 (1H, m); 7.50 (1H, m); 8.10 (1H, m); 8.75 (1H, m); 9.00 (1H, m).

EXAMPLE 40

17β-(2-Thiazolyl)androst-5-ene-3β,14β,17α-triol (I-bn)

To a solution of 7.40 g of thiazole in 600 ml of dry diethyl ether, cooled at −60° C., 44 ml of butyllithium (solution 1.6M in hexane) were added. After 2 hrs a solution of 2.00 g of 3β-hydroxy-14β-ethoxymethoxyandrosta-5,15-dien-17-one (II-a, Prep. 1) in 200 ml of dry diethyl ether was added and the mixture was stirred at −60° C. for 8 hrs. The reaction was allowed to rise to room temperature overnight and then was poured into water. The organic layer was dried over sodium sulrate and evaporated to dryness under reduced pressure. The crude product was purified by flash-chromatography (SiO$_2$) using ethyl acetate as eluant to give 1.10 g of 17β-(2-thiazolyl)-14β-ethoxymethoxyandrosta-5,15-diene-3β,17α-diol as a white solid.

$^1$H-NMR (300 MHz, CDCl$_3$, ppm from TMS): 0.80 (3H, s); 0.98 (3H, s); 3.40–3.62 (3H, m); 4.40 (1H, d); 4.50 (1H, d); 5.40 (1H, bs); 6.10 (1H, d); 6.45 (1H, d); 7.70 (1H, m); 8.70 (1H, m).

1.10 g of 17β-(2-thiazolyl)-14β-ethoxymethoxyandrosta-5,15-diene-3β,17α-diol were hydrogenated as described in Ex. 37 to give 1.0 g of 17β-(2-thiazolyl)-14β-ethoxymethoxyandrost-5-ene-3β,17α-diol.

$^1$H-NMR (300 MHz, CDCl$_3$, ppm from TMS): 0.70 (3H, s); 0.98 (3H, s); 2.40 (1H, m); 2.65 (1H, m); 3.25 (1H, dd); 3.49–3.65 (2H, m); 3.95 (1H, d); 4.60 (1H, d); 5.40 (1H, bs); 7.70 (1H, m); 8.70 (1H, m).

To a solution of 1.0 g 17β-(2-thiazolyl)-14β-ethoxymethoxyan-drost-5-ene-3β,17α-diol in 18 ml of acetonitrile and 2 ml of water, p-toluensulfonic acid was added until pH 1.1 was reached. After 20 hrs at room temperature the mixture was diluted with water and extracted with chloroform. The organic phase was dried over sodium sulfate and evaporated to dryness under reduced pressure. The crude product was purified by flash-chromatography (SiO$_2$) using chloroform/methanol/aqueous ammonia 89/10/1 as eluant to give 0.40 g of the title compound (I-bn) as a white solid.

$^1$H-NMR (300 MHz, CDCl$_3$, ppm from TMS): 0.70 (3H, s); 0.98 (3H, s); 2.35 (1H, m); 2.70 (1H, m); 3.49–3.62 (1H, m); 5.40 (1H, bs); 7.70 (1H, m); 8.70 (1H, m).

EXAMPLE 41

17β)-(1,2-Dimethyl-5-imidazolyl)androst-5-ene-3β,14β,17α-triol (I-bo)

The title compound (I-bo) (0.20 g) was obtained as a white solid from 5.10 g of 3β-hydroxy-14β-ethoxymethoxyandrosta-5,15-dien-17-one (II-a, Prep. 1), using the same procedure described in Ex. 40 and 1,2-dimethylimidazole.

$^1$H-NMR (300 MHz, CDCl$_3$, ppm from TMS): 0.70 (3H, s); 0.98 (3H, s); 2.35 (1H, m); 2.40 (3H, s); 2.70 (1H, m); 3.49–3.65 (4H, m); 5.40 (1H, bs); 7.00 (1H, m).

EXAMPLE 42

17β-(4-(N,N-Dimethylaminophenyl))androst-5-ene-3β,14β,17α-triol (I-bp)

The title compound (I-bp) (0.28 g) was obtained as a white solid from 1.20 g of 3β-hydroxy-14β-ethoxymethoxyandrosta-5,15-dien-17-one (II-a, Prep.1), using the same procedure described in Ex. 40 and 4-bromo-N,N-dimethylaniline.

$^1$H-NMR (300 MHz, CDCl$_3$, ppm from TMS): 0.70 (3H, s); 0.98 (3H, s); 2.35 (1H, m); 2.70 (1H, m); 3.49–3.62 (1H, m); 5.40 (1H, bs); 6.80 (2H, m); 7.20 (2H, m).

EXAMPLE 43

17β-(2-Furyl)androst-5-ene-3β,14β,17α-triol (I-bq)

The title compound (I-bq) (0.22 g) was obtained as a white solid from 1.50 g of 3β-hydroxy-14β-ethoxymethoxyandrosta-5,15-dien-17-one (II-a, Prep. 1) and furan, using the same procedure described in Ex. 40 and carrying out the hydrogenation over Raney Nickel.

$^1$H-NMR (300 MHz, CDCl$_3$, ppm from TMS): 0.70 (3H, s); 0.98 (3H, s); 2.35 (1H, m); 2.70 (1H, m); 3.49–3.62 (1H, m); 5.40 (1H, bs); 6.30 (2H, m); 7.30 (1H, m).

EXAMPLE 44

3β-(2-(1-Pyrrolidinyl)ethoxy)-17β-(3-furyl)androst-4-ene-14β,17α-diol (I-br)

To a suspension of 0.080 g of NaH (60% dispersion in mineral oil) in 8 ml of dry tetrahydrofuran, 0.27 g of 17β-(3-furyl)androst-4-ene-3β,14β,17α-triol (I-ah) were added at room temperature, under nitrogen atmosphere. The mixture was refluxed for 3 hrs, then 0.67 g of 1-(2-chloroethyl)pyrrolidine were added; the suspension was refluxed for 2 hrs; 10 ml of water were added cautiously and the tetrahydrofuran was distilled at reduced pressure. The residue was extracted with methylene chloride, the organic layer was dried over anhydrous sodium sulfate and evaporated to dryness, under reduced pressure. The crude product was purified by flash-chromatography (SiO$_2$) using methylene chloride/methanol 90/10 as eluant to give 0.037 g of the title compound (I-br) as a white solid.

$^1$H-NMR (300 MHz, CDCl$_3$, ppm from TMS): 0.85 (3H, s); 0.95 (3H, s); 2.52–2.70 (6H, m); 3.64–3.77 (2H, m); 3.62 (1H, bs); 5.32 (1H, bs); 6.53 (1H, bs); 7.35(1H, bs); 7.42 (1H, bs).

EXAMPLE 45

3β-(2-(2-(1-Pyrrolidinyl)ethoxy)ethoxy)-17β-(3-furyl)androst-4-ene-14β,17α-diol (I-bs)

To a solution of 1.34 g of 3β-(2-hydroxyethoxy)-17β-(3-furyl)androst-4-ene-14β,17α-diol (I-ai), in 6 ml of dry pyridine, 0.57 g of tosyl chloride were slowly added at room temperature. After 5 hrs stirring, 15 ml of water and 60 ml of ethyl acetate were added. the organic layer was washed with water and dried over sodium sulfate to give 1.5 g of 3β-(2-tosyloxyethoxy)-17β-(3-furyl)androst4-ene-14β,17α-diol as awhite solid.

$^1$H-NMR (300 MHz, CDCl$_3$, ppm from TMS): 0.85 (3H, s); 0.97 (3H, s); 2.48 (3H, s); 3.52–3.62 (2H, m); 3.67–3.80 (1H, m); 4.15–4.20 (2H, M); 5.32 (1H, bs); 6.53 (1H, bs); 7.30–7.38 (3H, m); 7.42 (1H, bs); 7.78–7.83 (2H, d).

To a suspension of 0.24 g of NaH (60% dispersion in mineral oil) in 30 ml of anhydrous dimethylformamide, 0.35 g of 1-(2-hydroxyethyl)pyrrolidine were added at room temperature in a nitrogen atmosphere: after 2 hrs, 1.25 g of 3β-(2-tosyloxyethoxy)-17β-(3-furyl)androst-4-ene-14β,17α-diol were added. After 4 hrs, 30 ml of water were added cautiously. The residue was extracted with methylene chloride, the organic layer was washed with water, dried over sodium sulfate and evaporated to dryness under reduced pressure. The crude product was purified by flash-chromatography (SiO$_2$) using methylene chloride/methanol 95/5 as eluant to give 0.95 g of the title compound (I-bs) as a light yellow solid.

$^1$H-NMR (300 MHz, CDCl$_3$, ppm from TMS): 0.85 (3H, s); 0.97 (3H, s); 2.52–2.67 (4H, m); 2.67–2.78 (2H, m); 3.51–3.58 (2H, m); 3.58–3.80 (5H, m); 5.32 (1H, bs); 6.53 (1H, bs); 7.37 (1H, bs); 7.42 (1H, bs).

EXAMPLE 46

3β-(2-Methylaminoethoxy)-17β-(3-furyl)androst-4-ene-14β,17α-diol (I-bt)

To 18 ml of a solution of methylamine 3.2M in methanol, 0.30 g of 3β-(2 -tosyloxyethoxy)-17β-(3-furyl)androst-4-ene- 14β,17α-diol, prepared as an intermediate in Ex. 45, were added. The solution was kept at reflux temperature under nitrogen atmosphere for 11 hrs and then evaporated to dryness under reduced pressure. The resulting solid was washed with n-hexane to give 0.16 g of the title compound (I-bt) as a light yellow pasty solid.

$^1$H-NMR (300 MHz, CDCl$_3$, ppm from TMS): 0.85 (3H, s); 0.97 (3H, s); 2.54 (3H, s); 2.82 (2H, t); 3.00–3.08 (2H, m); 3.68–3.80 (1H, m); 5.32 (1H, bs); 6.53 (1H, s); 7.37 (1H, s); 7.42 (1H, s).

EXAMPLE 47

3β-(3-Guanidinopropoxy)-17β-(3-furyl)androst-4-ene-14β,17α-diol (I-bu)

To a solution of 0.43 g of 3β-(3-aminopropoxy)-17β-(3-furyl)androst-4-ene-14β,Jα-diol (I-aj) in 20 ml of absolute ethanol 0.35 g of 3,5-dimethyl-1-pyrazolylformamidinium nitrate were added and the mixture was kept at reflux temperature for 24 hrs; the ethanol was concentrated under reduced pressure and 0.39 g of the title compound (I-bu) crystallized as a white solid.

$^1$H NMR: (300 MHz, DMSO-d6, ppm from TMS): 0.70 (3H, s); 1.03 (3H, s); 3.14 (2H, m); 3.35 (2H, m); 3.54–3.65 (1H, m); 3.82 (1H, bs); 5.32 (1H, bs); 6.56 (1H, bs); 7.42 (1H, bs); 7.55 (1H, bs).

EXAMPLE 48

3β-((2RS)-2,3-Dihydroxypropoxy)-17β-(3-furyl)androst-4-ene-14β,17α-diol (I-bv)

To a mixture of 0.84 g of N-methylmorpholine-N-oxide, 7 ml of water, 15 ml of acetone and 2 ml of a 0.06M ethereal osmium tetroxide solution, 2.5 g of 3β-(prop-2-enoxy)-17β-(3-furyl)androst-4-ene-14β,17α-diol, prepared as described in Ex. 4, dissolved in 33 ml of tert-butanol were added at room temperature. The mixture was left on standing for 20 hrs, 50 ml of a saturated sodium hydrosulfite solution and 3 g of celite were added, the mixture was stirred for 2 hrs and then filtered. The organic solvent was distilled under reduced pressure, the aqueous phase was extracted with methylene chloride, the organic layer was dried over sodium sulfate and evaporated to dryness under reduced pressure. The crude product was purified by flash-chromatography (SiO$_2$) using n-hexane/ethyl acetate 20/80 as eluant to give 2.2 g of the title compound (I-bv) as a white solid.

$^1$H NMR (300 MHz, CDCl$_3$, ppm from TMS): 0.85 (3H, s); 1.03 (3H, s); 3.46–3.60 (2H, m): 3.67–3.79 (3H, m); 3.82–3.92 (1H, m); 5.32 (1H, bs); 6.53 (1H, bs); 7.37 (1H, bs): 7.42 (1H, bs).

EXAMPLE 49

3β-((2RS)-2,3-Diaminopropoxy)-17β-(3-furyl)-androst-4-ene-14β,17α-diol (I-bw)

To a solution of 0.82 g of 3β-((2RS)-2,3-dihydroxypropoxy)-17β-(3-furyl)androst-4-ene-14β,17α-diol (I-bv), in 6.4 ml of dry pyridine, 0.8 g of tosyl chloride were added at a temperature of 0° C. After 5 hrs 15 ml of water and 60 ml of ethyl acetate were added, the organic layer was washed with water, dried over sodium sulfate and evaporated to dryness under reduced pressure. The crude product was purified by flash-chromatography (SiO$_2$) using n-hexane/ethyl acetate 80/20 as eluant to give 1.2 g of 3β-((2RS)-2,3-ditoxyloxypropoxy)-17β-(3-furyl)androst-4-ene-14β,17α-diol as a white solid.

$^1$H NMR (300 MHz, CDCl$_3$, ppm from TMS): 0.85 (3H, s); 0.93 (3H, s); 2.45 (6H, bs): 3.40–3.61 (2H, m); 3.67–3.77 (1H, bs); 4.05–4.18 (2H, m); 4.62 (1H, bs); 5.32 (1H, bs); 6.58 (1H, bs); 7.30–7.43 (6H, m); 7.70–7.82 (4H, m).

To a solution of 1.2 g of 3β-((2RS)-2,3-ditosyloxypropoxy)-17β-(3-furyl)androst-4-ene-14β,17α-diol in 9 ml of dimethylsulfoxide 1 g of sodium azide were added at room temperature. The solution was kept at reflux temperature for 3 hrs, then 5 ml of water were added and the residue was extracted with methylene chloride. The organic layer was washed with water, dried over sodium sulfate and evaporated to dryness under reduced pressure. The crude product was purified by flash-chromatography (SiO$_2$) using n-hexane/ethyl acetate 80/20 as eluant to give 0.7 g 3β-((2RS)-2,3-diazidopropoxy)-17β-(3-furyl)androst-4-ene-14β,17α-diol.

$^1$H NMR: (300 MHz, CDCl$_3$, ppm from TMS): 0.86 (3H, s); 0.94 (3H, s); 3.4–3.78 (6H, m); 5.32 (1H, bs); 6.53 (1H, bs); 7.37 (1H, bs); 7.42 (1H, bs).

A solution of 0.42 g of 3β-((2RS)-2,3-diazidopropoxy)-17β-(3-furyl)androst-4-ene-14β,17α-diol in 10 ml of diethyl ether was added to a suspension of 0.15 g of lithium aluminum hydride in 6 ml of diethyl ether. The mixture was kept at reflux temperature for 12 hrs then in succession 0.32 ml of water, 0.32 ml of sodium hydroxyde (water solution 10%) and 1.5 ml of water were added. The mixture was filtered over a celite cake, the organic solution was washed with water, dried over sodium sulfate and evaporated to dryness under reduced pressure. The crude residue was purified by flash-chromatography (SiO$_2$) using methylene chloride/methanol/30% ammonia solution 90/10/1 as eluant to give 0.34 g of the title compound (I-bw) a white solid.

$^1$H NMR (300 MHz, CDCl$_3$, ppm from TMS): 0.84 (3H, s); 0.90 (3H, s); 2.70–3.50 (5H, m): 3.68–3.77 (1H, m); 5.32 (1H, bs); 6.53 (1H, bs); 7.37 (1H, bs); 7.42 (1H, bs).

EXAMPLE 50

3β-Mercapto-17β-(3-furyl)androst-4-ene-14β,17α-diol (I-bx)

Diisopropyl azodicarboxylate (8.9 ml) was added to a solution of 11.2 g of triphenylphosphine in 200 ml of tetrahydrofuran at 0° C. and the mixture was stirred for 30'. To this mixture a solution of 5.0 g of 17β-(3-furyl)androst-4-ene-3β,14β,17α-triol (I-ah) and 5.20 ml of thiolacetic acid in 250 ml of tetrahydrofuran was added dropwise and the resulting mixture was stirred for one hr at room temperature. The solvent was evaporated to dryness under reduced pressure and the crude product was purified by flash-chromatography (SiO$_2$) using n-hexane/ethyl acetate 95/5 as eluant to give 4.2 g of 3β-acetylthio-17β-(3-furyl)androst-4-ene-14β,17α-diol as a white solid.

$^1$H-NMR (300 MHz, CDCl$_3$ ppm from TMS): 0.80 (3H, s); 1.05 (3H, s); 2.25–2.35 (3H, m); 4.08 (1H, bs); 5.35 (1H, bs); 6.53 (1H, bs); 7.35 (1H, bs); 7.42 (1H, bs).

A solution of 4.0 g of 3β-acetylthio-17β-(3-furyl)androst-4-ene-14β,17α-diol in 50 ml of methanol, was saturated with gaseous ammonia and kept for 3 hrs at room temperature. The mixture was evaporated to dryness under reduced pressure and purified by flash-chromatography (SiO$_2$) using n-hexane/ethyl acetate 95/5 as eluant to give 3.2 g of the title compound (I-bx) as a white solid.

$^1$H-NMR (300 MHz, CDCl$_3$ ppm from TMS): 0.80 (3H, s); 1.05 (3H, s); 3.62 (1H, bs); 5.35 (1H, bs); 6.53 (1H, bs); 7.35 (1H, bs); 7.42 (1H, bs).

EXAMPLE 51

3β-(3-Aminopropylthio)-17β-(3-furyl)androst-4-ene-14β,17α-diol (I-by)

To a solution of 1.14 g of 3β-mercapto-17β-(3-furyl)androst-4-ene-14β,17α-diol (I-bx) and 0.67 ml of 3-chloropropylamine in 10 ml of tetrahydrofuran under nitrogen atmosphere, at room temperature, 0.063 g of sodium hydride (60% dispersion in mineral oil) were added.

The reaction mixture xvas stirred for 40 hrs at room temperature then diluted with water and extracted with ethyl acetate. The organic layer was dried over sodium sulfate and evaporated to dryness under reduced pressure. The crude product was purified by flash-chromatography (SiO$_2$) using methylene chloride/methanol/30% ammonia solution 95/5/1 as eluant to give 0.35 g of the title compound (I-by) as a white solid.

$^1$H-NMR (300 MHz, CDCl$_3$ ppm from TMS): 0.80 (3H, s); 1.05 (3H, s); 2.51–2.64 (2H, m); 2.83 (2H, bt); 3.22 (1H, bs); 5.35 (1H, bs); 6.53 (1H, bs); 7.35 (1H, bs); 7.42 (1H, bs).

EXAMPLE 52

3β-(2-(1-Pyrrolidinyl)ethylthio)-17β-(3-furyl) androst-4-ene-14β,17α-diol (I-bz)

The title compound (I-bz) (0.29 g) was obtained as a pale yellow solid from 0.35 g of 3β-mercapto-17β-(3-furyl) androst-4-ene-14β,17α-diol (I-bx) and 1-(2-chloroethyl) pyrrolidine (0.73 g) using the same procedure described in Ex. 51.

$^1$H-NMR (300 MHz, CDCl$_3$ ppm from TMS): 0.80 (3H, s); 1.05 (3H, s); 2.51–2.61 (4H, m); 2.65–2.69 (4H, bt); 3.22 (1H, bs); 5.35 (1H, bs); 6.53 (1H, bs); 7.35 (1H, bs); 7.42 (1H, bs).

PREPARATION OF INTERMEDIATES

Preparation 1

3β-Hydroxy-14β-ethoxymethoxyandrosta-5,15-dien-17-one (II-a)

A solution of 9.20 g of 3β-acetoxy-14β-hydroxyandrosta-5,15-dien-17-one (G. Groszek et al., *Bull. Pol. Acad. Sci., Chem.*, 34, 1986, 313), 11 ml of ethyl chloromethyl ether, 54 ml of diisopropylethylamine in 750 ml of dichloromethane was heated at reflux for 24 hrs. The solution was then cooled and poured into 500 ml of aq. 8% citric acid solution. The lower layer was separated, washed with water, dried over sodium sulfate and avaporated to dryness. The crude product was purified by chromatography using cyclohexane/chloroform/acetone 80/10/10 as eluant to give 6.10 g of 3β-acetoxy-14β-ethoxymethoxyandrosta-5,15-dien-17-one as a white solid.

$^1$H-NMR (300 MHz, CDCl$_3$, ppm from TMS): 0.90 (3H, s); 1.07 (3H, s); 2.00 (3H, s); 3.40–3.51 (IH, m): 3.78–3.88 (1H, m); 4.48 (1H, d); 4.52 (1H, d); 5.08–5.15 (1H, m); 5.42 (1H, bs); 6.42 (1H, d); 7.79 (1H, d).

A solution of 6.00 g of 3β-acetoxy-14β-ethoxymethoxyandrosta-5,15-dien-17-one and 30 ml of 2N aq. sodium hydroxide in 120 ml of methanol was kept at room temperature for 24 hrs. The mixture was then diluted with water and extracted with dichloromethane. The organic phase was dried over sodium sulfate and evaporated to dryness to give 4.90 g of the title compound (II-a) as a white solid.

$^1$H-NMR (300 MHz, CDCl$_3$, ppm from TMS): 0.90 (3H, s); 1.07 (3H, s); 3.40–3.51 (2H, m); 3.78–3.88 (1H, m); 4.43 (1H, d); 4.52 (1H, d); 5.42 (1H, bs); 6.42 (1H, d); 7.79 (1H, d).

Preparation 2

3β-Hydroxy-14β-ethoxymethoxy-5α-androst-15-en-17-one (II-b)

The title compound (II-b) (6.90 g) was obtained as a light yellow oil from 3β,14β-dihydroxy-5α-androst-15-en-17-one (U.S. Pat. No. 3,595,883) (10.00 g) using the same procedure described in Prep. 1.

$^1$H-NMR (300 MHz, CDCl$_3$, ppm from TMS): 0.79 (3H, s); 0.90 (3H, s); 3.40–3.68 (2H, m); 3.78–3.88 (1H, m); 4.43 (1H, d); 4.52 (1H, d); 6.42 (1H, d); 7.79 (1H, d).

We claim:

1. 17-Aryl-5α,14β-androstane, androstene and androstadiene derivatives of formula (I):

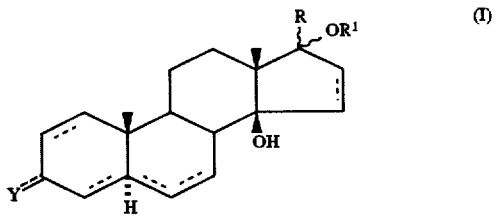

wherein:

the symbol ⁓ means that the substituents in position 17 have an α or β configuration;

the symbol ═ represents a single or a double bond; when the double bond is not present in the 4 or 5 position, the hydrogen in position 5 has the α configuration;

Y is oxygen or guanidinoimino, when ═ in position 3 is a double bond;

Y is hydroxy, OR$^2$ or SR$^2$, when ═ in position 3 is a single bond and has an α or β configuration;

R is an aryl ring, unsubstituted or substituted by one or more halogen, hydroxy, hydroxymethyl, alkoxy, oxo, amino, alkylamino, dialkylamino, cyano, nitro, sulfonamido, C1–C6 lower alkyl group or COR$^3$;

R$^1$ is hydrogen; methyl; ethyl or n-propyl substituted by OH or NR$^4$R$^5$;

R$^2$ is hydrogen; methyl; C2–C6 alkyl or C3–C6 alkenyl or C2-6-alkanuyl acyl, each of which is optionally substituted by one or more of OR$^6$, NR$^7$R$^8$, CHO, C(NH)NH$_2$, guanidinoimino or by NR$^7$R$^8$ and hydroxy;

R$^3$ is hydrogen, hydroxy, C1–C4 alkoxy or C1–C4 alkyl;

R$^4$, R$^5$ are independently hydrogen; methyl; C2–C6 alkyl unsubstituted or substituted by NR$^9$R$^{10}$, or R$^4$ and R$^5$ taken together with the nitrogen atom form an unsubstituted or substituted, saturated or unsaturated five- or six-membered heterocyclic ring, optionally containing another heteroatom selected from the group consisting of oxygen, sulfur and nitrogen;

R$^6$ is hydrogen; methyl; C2–C4 alkyl unsubstituted or substituted by one or more NR$^9$R$^{10}$ groups, or by NR$^9$R$^{10}$ and hydroxy;

R$^7$, R$^8$ are independently hydrogen; methyl; C2–C6 alkyl or C3–C6 alkenyl unsubstituted or substituted by one or more NR$^9$R$^{10}$, or NR$^9$R$^{10}$ and hydroxy, or R$^7$ and R$^8$ taken together with the nitrogen atom form an unsubstituted or substituted, saturated or unsaturated five- or six-membered heterocyclic ring, optionally containing another heteroatom selected from the group consisting of oxygen, sulfur and nitrogen, or R$^7$ is hydrogen and R$^8$ is C(NH)NH$_2$;

R$^9$, R$^{10}$ are independently hydrogen, C1–C6 alkyl, or R$^9$ and R$^{10}$, taken together with the nitrogen atom they are linked to form a saturated or unsaturated five- or six-membered heterocyclic ring and the stereoisomers, in particular Z and E isomers, optical isomers and their mixtures and the metabolites and the metabolic precursors of the compounds of formula (I).

2. A pharmaceutically acceptable salt of a compound of formula (I).

3. A compound according to claim 1, which is selected from the group consisting of:
17β-Phenyl-5α-androst-1-ene-3β,14β,17α-triol,
17β-(4-Methoxyphenyl)-5α-androst-1-ene-3β,14β,17α-triol,
17β-Phenylandrosta-4,15-diene-3β,14β,17α-triol,
3β-(2(1-Pyrrolidinyl)ethoxy)-17β-phenylandrosta-4,15-diene-14β,17α-diol,
17β-Phenylandrost-4-ene-3β,14β,17α-triol,
3β-(2-(1-Pyrrolidinyl)ethoxy)-17β-phenylandrost-4-ene-14β,17α-diol,
17β-Phenyl-17α-(2-(1-pyrrolidinyl)ethoxy)androst-4-ene-3β,14β-diol,
3β,17α-Bis(2-(1-pyrrolidinyl)ethoxy)-17β-phenylandrost-4-en-14β-ol,
17β-(4-Methoxyphenyl)androsta-4,15-diene-3β,14β,17α-triol,
3β-(2-(1-Pyrrolidinyl)ethoxy)-17β-(4-methoxyphenyl)androsta-4,15-diene-14β,17α-diol,
17β-(4-Methoxyphenyl)androst-4-ene-3β,14β,17α-triol,
3β-(2-(1-Pyrrolidinyl)ethoxy)-17β-(4-methoxyphenyl)androst-4-ene-14β,17α-diol,
17β-(4-Methoxyphenyl)-17α-(2-(1-pyrrolidinyl)ethoxy)androst-4-ene-3β,14β-diol,
3β,17α-Bis(2-(1-pyrrolidinyl)ethoxy)-17β-(4-methoxyphenyl)androst-4-en-14β-ol,
17β-(4-Chlorophenyl)androst-4-ene-3β,14β,17α-triol,
17β-(4-(N,N-Dimethylaminophenyl))androst-4-ene-3β,14β,17α-triol,-
(4-Carboxyphenyl)androst-4-ene-3β,14β,17α-triol,
17β-Phenylandrosta-5,15-diene-3β,14β,17α-triol,
17β-Phenylandrost-5-ene-3β,14β,17α-triol,
3β-(2-(1-Pyrrolidinyl)ethoxy)-17β-phenylandrost-5-ene-14β,17α-diol,
17β-Phenyl-17α-(2-(1-pyrrolidinyl)ethoxy)androst-5-ene-3β,14β-diol,
3β,17α-Bis(2-(1-pyrrolidinyl)ethoxy)-17β-phenylandrost-5-en-14β-ol,
17β-(4-Methoxyphenyl)androst-5-ene-3β,14β,17α-triol,
3β-(2-(1-Pyrrolidinyl)ethoxy)-17β-(4-methoxyphenyl)androst-5-ene-14β,17α-diol,
17β-(4-Methoxyphenyl)-17α-(2-(1-pyrrolidinyl)ethoxy)androst-5-ene-3β,14β-diol,
3β,17α-Bis(2-(1-pyrrolidinyl)ethoxy)-17β-(4-methoxyphenyl)androst-5-en-14β-ol,
17β-4-Chlorophenyl)androst-5-ene-3β,14β,17α-triol,
17β-(4-(N,N-Dimethylaminophenyl))androst-5-ene-3β,14β,17α-triol,
17β-(4-Carboxyphenyl)androst-5-ene-3β,14β,17α-triol,
17β-Phenylandrosta-4,6-diene-3β,14β,17α-triol,
17β-(4-Methoxyphenyl)androsta-4,6-diene-3β,14β,17α-triol,
17β-Phenyl-5α-androst-15-ene-3β,14β,17α-triol,
3β-(2-(1-Pyrrolidinyl)ethoxy)-17β-phenyl-5α-androst-15-ene-14β,17α-diol,
17β-Phenyl-5α-androstane-3β,14β,17α-triol,
3β-(2-(1-Pyrrolidinyl)ethoxy)-17β-phenyl-5α-androstane-14β,17α-diol,
17β-Phenyl-17α-(2-(1-pyrrolidinyl)ethoxy)-5α-androstane-3β,14β-diol,
3β,17α-Bis(2-(1-pyrrolidinyl)ethoxy)-17β-phenyl-5α-androstan-14β-ol,
17β-(4-Methoxyphenyl)-5β-androstane-3β,14β,17α-triol,
3β-(2-(1-Pyrrolidinyl)ethoxy)-17β-(4-methoxyphenyl)-5α-androstane-14β,17α-diol,
17β-(4-Methoxyphenyl)-17β-(2-(1-pyrrolidinyl)ethoxy)-5α-androstane-3β,14β-diol,
3α,17α-Bis(2-(1-pyrrolidinyl)ethoxy)-17β-(4-methoxyphenyl)-5α-androstan-14β-ol,
17β-(4-Chlorophenyl)-5α-androstane-3β,14β,17α-triol,
17β-(4-(N,N-Dimethylaminophenyl))-5α-androstan-3β,14β,17α-triol,
17β-(4-Carboxyphenyl)-5α-androstane-3β,14β,17α-triol;

and the corresponding 3β-(2-hydroxyethoxy), 3β-(3-hydroxypropoxy), 3β-(2,3-dihydroxypropoxy), 3β-(2-aminoethoxy), 3β-(3-aminopropoxy), 3β-(2-methylaminoethoxy), 3β-(3-methylaminopropoxy), 3β-(2-dimethylaminoethoxy), 3β-(3-dimethylaminopropoxy), 3β-(2-diethylaminoethoxy), 3β-(3-diethylaminopropoxy), 3β-(3-(1-pyyrolidinyl)propoxy), 3β-(2,3-diaminopropoxy), 3β-(2-(2-(1-pyrrolidinyl)ethoxy), 3β-(2-guanidinoethoxy), 3β-(3-guanidinopropoxy) of the 3β-(2-(1-pyrrolidinyl)ethoxy) derivatives;

and the corresponding 17α-(2-hydroxyethoxy), 17α-(3-hydroxypropoxy), 17α-(2-aminoethoxy), 17α-(3-aminopropoxy), 17α-(3-(1-pyrrolidinyl)propoxy) of the 17α-(2-(1-pyrrolidinyl)ethoxy) derivatives;

and the corresponding 3β,17α-bis(2-hydroxyethoxy), 3β,17α-bis(3-hydroxypropoxy), 3β,17α-bis(2-aminoethoxy), 3β,17α-bis(3-aminopropoxy), 3β,17α-bis(3-(1-pyrrolidinyl)propoxy) of the 3β,17α-bis(2-(1-pyrrolidinyl)ethoxy) derivatives;

and the corresponding 3-oxo and 3-guanidinoimino of the corresponding 3β-ol derivatives;

and the corresponding 3β-(2-aminoethylthio), 3β-(3-aminopropylthio), 3β-(2-(1-pyrrolidinyl)ethylthio), 3β-(3-(1-pyrrolidinyl)propylthio), 3β-(2-(2-(1-pyrrolidinyl)ethoxy)ethylthio) of the 3β-(2-(1-pyrrolidinyl)ethoxy) derivatives.

4. A pharmaceutical composition, comprising:
a therapeutically effective amount of the compound of claim 1 in combination with a pharmaceutically acceptable carrier and/or diluent.

* * * * *

UNITED STATES PATENT AND TRADEMARK OFFICE
CERTIFICATE OF CORRECTION

PATENT NO. : 5,721,227
DATED : February 24, 1998
INVENTOR(S): Piero MELLONI, et al.

It is certified that error appears in the above-identified patent and that said Letters Patent is hereby corrected as shown below:

On the title page, item [*] should be:

-- [*]  Notice:  The term of this patent shall not extend beyond the expiration date of Pat. No. 5,567,694.--

Signed and Sealed this

Twenty-eighth Day of April, 1998

Attest:

BRUCE LEHMAN

Attesting Officer

Commissioner of Patents and Trademarks